US011378430B2

(12) United States Patent
Ruchti et al.

(10) Patent No.: US 11,378,430 B2
(45) Date of Patent: Jul. 5, 2022

(54) AIR DETECTION SYSTEM AND METHOD FOR DETECTING AIR IN A PUMP OF AN INFUSION SYSTEM

(71) Applicant: ICU Medical, Inc., San Clemente, CA (US)

(72) Inventors: Timothy L. Ruchti, Gurnee, IL (US); Brian G. Markey, Park Forest, IL (US); Anatoly S. Belkin, Glenview, IL (US); Paul T. Kotnik, Commerce Township, MI (US); Mohammad M. Khair, Streamwood, IL (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 16/806,967

(22) Filed: Mar. 2, 2020

(65) Prior Publication Data

US 2020/0271499 A1 Aug. 27, 2020

Related U.S. Application Data

(63) Continuation of application No. 16/001,680, filed on Jun. 6, 2018, now Pat. No. 10,578,474, which is a (Continued)

(51) Int. Cl.

| | |
|---|---|
| ***G01F 1/74*** | (2006.01) |
| ***A61M 5/168*** | (2006.01) |

(Continued)

(52) U.S. Cl.

CPC ........... *G01F 1/74* (2013.01); *A61M 5/16831* (2013.01); *A61M 5/365* (2013.01);

(Continued)

(58) Field of Classification Search

None

See application file for complete search history.

(56) References Cited

U.S. PATENT DOCUMENTS

| | | | |
|---|---|---|---|
| 3,894,431 | A | 7/1975 | Muston et al. |
| 4,480,483 | A | 11/1984 | McShane |

(Continued)

FOREIGN PATENT DOCUMENTS

| | | |
|---|---|---|
| AU | 2013216679 | 9/2013 |
| EP | 1 490 131 | 12/2007 |

(Continued)

OTHER PUBLICATIONS

"Decision of the Administrative Council of Oct. 16, 2013 Amending Rule 135 and 164 of the Implementing Regulations to the European Patent Convention (CA/D 17/13)", Official Journal EPO Nov. 2013, Nov. 2013, pp. 503-506. http://archive.epo.org/epo/pubs/o1013/11_13/11_5033.pdf.

(Continued)

*Primary Examiner* — Lina M Cordero

(74) *Attorney, Agent, or Firm* — Knobbe Martens Olson & Bear, LLP

(57) ABSTRACT

Various systems and methods for detecting air in a chamber of an infusion system are disclosed. In one embodiment, a determination is made that air is contained in the chamber on the basis of a change in the average force exerted against the plunger utilizing a derivative spike for event detection and a systematic reduction in the average force to confirm the nature of the change. In another embodiment, a determination is made that the chamber contains air when a difference between the current force profile and a baseline force profile crosses a threshold. In an additional embodiment, a force profile is classified as being an air force profile or a liquid force profile based on extracted features of the force profile.

14 Claims, 19 Drawing Sheets

Related U.S. Application Data continuation of application No. 13/851,207, filed on Mar. 27, 2013, now Pat. No. 9,995,611.

(60) Provisional application No. 61/618,129, filed on Mar. 30, 2012.

(51) Int. Cl.
*A61M 5/36* (2006.01)
*F04B 43/00* (2006.01)
*F04B 51/00* (2006.01)

(52) U.S. Cl.
CPC .......... *F04B 43/0081* (2013.01); *F04B 51/00* (2013.01); *A61M 2205/331* (2013.01)

(56) References Cited

U.S. PATENT DOCUMENTS 5,304,216 A 4/1994 Wallace
5,325,170 A 6/1994 Bornhop
6,142,008 A * 11/2000 Cole .................... A61M 5/365 128/DIG. 13
6,358,387 B1 3/2002 Kopf-Sill et al.
7,087,444 B2 8/2006 Wong et al.
7,347,854 B2 3/2008 Shelton et al.
7,477,997 B2 * 1/2009 Kaplit .................... B01L 3/021 221/10
7,981,082 B2 * 7/2011 Wang ................ A61M 5/16831 604/122
8,002,736 B2 8/2011 Patrick et al.
8,197,444 B1 * 6/2012 Bazargan .......... A61M 5/16854 604/131
8,221,395 B2 7/2012 Shelton et al.
8,318,094 B1 11/2012 Bayandorian et al.
8,469,942 B2 * 6/2013 Kow ................ A61M 5/14244 604/503
8,477,307 B1 7/2013 Yufa et al.
8,523,797 B2 9/2013 Lowery et al.
8,728,020 B2 * 5/2014 Caleffi ............. A61M 5/16845 604/5.01
9,545,475 B2 1/2017 Borges et al.
9,764,087 B2 9/2017 Peterfreund et al.
9,852,265 B1 12/2017 Treacy et al.
10,022,498 B2 7/2018 Ruchti et al.
10,046,112 B2 8/2018 Oruklu et al.
10,089,055 B1 10/2018 Fryman
10,166,328 B2 1/2019 Oruklu et al.
10,342,917 B2 7/2019 Shubinsky et al.
10,430,761 B2 10/2019 Hume et al.
10,463,788 B2 11/2019 Day
10,578,474 B2 3/2020 Ruchti et al.
10,596,316 B2 3/2020 Dumas, III et al.
2002/0031838 A1 3/2002 Meinhart et al.
2002/0038392 A1 3/2002 de la Huerga
2002/0169636 A1 11/2002 Eggers et al.
2003/0052787 A1 3/2003 Zerhusen et al.
2003/0114836 A1 6/2003 Estes et al.
2003/0135388 A1 7/2003 Martucci et al.
2003/0186833 A1 10/2003 Huff et al.
2003/0194328 A1 10/2003 Bryant et al.
2003/0216682 A1 11/2003 Junker
2005/0137653 A1 6/2005 Friedman et al.
2005/0197649 A1 9/2005 Shelton et al.
2005/0204828 A1 9/2005 Lee et al.
2006/0026205 A1 2/2006 Butterfield et al.
2006/0047538 A1 3/2006 Condurso et al.
2006/0224140 A1 10/2006 Junker
2006/0229551 A1 10/2006 Martinez et al.
2007/0036511 A1 2/2007 Lundquist et al.
2007/0088271 A1 4/2007 Richards
2007/0299389 A1 12/2007 Halbert et al.
2009/0105636 A1 4/2009 Hayter et al.
2009/0114037 A1 5/2009 Smith
2010/0114027 A1 5/2010 Jacobson et al.
2010/0185182 A1 7/2010 Alme et al.
2010/0256562 A1 10/2010 Cartledge et al.
2010/0271218 A1 10/2010 Hoag et al.
2010/0317952 A1 12/2010 Budiman et al.
2011/0064612 A1 * 3/2011 Franzoni ............. A61M 5/1689 422/44
2011/0071844 A1 3/2011 Cannon et al.
2011/0106561 A1 5/2011 Eaton, Jr. et al.
2011/0218514 A1 9/2011 Rebours
2011/0313390 A1 12/2011 Roy et al.
2012/0323212 A1 12/2012 Murphy
2013/0012880 A1 1/2013 Blomquist
2013/0197930 A1 8/2013 Garibaldi et al.
2013/0274576 A1 10/2013 Amirouche et al.
2013/0281965 A1 10/2013 Kamen et al.
2014/0180711 A1 6/2014 Kamen et al.
2014/0303591 A1 10/2014 Peterfreund et al.
2015/0065988 A1 3/2015 Holderle et al.
2015/0224252 A1 8/2015 Borges et al.
2016/0151601 A1 6/2016 Cardelius et al.
2016/0193604 A1 7/2016 McFarland et al.
2016/0339167 A1 11/2016 Ledford et al.
2018/0018440 A1 1/2018 Sugawara
2019/0091401 A1 3/2019 Ruchti et al.
2019/0117890 A1 4/2019 Oruklu et al.
2019/0196770 A1 6/2019 Fryman
2019/0262535 A1 8/2019 Shubinsky et al.
2019/0282757 A1 9/2019 Gylland et al.
2020/0069864 A1 3/2020 Shubinsky et al.

FOREIGN PATENT DOCUMENTS

JP 07-502678 3/1995
JP 2000-515716 11/2000
JP 2002-506514 2/2002
JP 2007-520270 7/2007
JP 2010-063767 3/2010
WO WO 96/028209 9/1996
WO WO 2004/070556 8/2004
WO WO 2008/019016 2/2008
WO WO 2009/141504 11/2009
WO WO-2011080188 A1 * 7/2011 .......... A61M 1/3659
WO WO 2012/082599 6/2012
WO WO 2012/108910 8/2012
WO WO 2012/167090 12/2012

OTHER PUBLICATIONS

"Decision of the Administrative Council of Oct. 27, 2009 Amending the Implementing Regulations to the European Patent Convention (CA/D 20/09)", Official Journal EPO Dec. 2009, Dec. 2009, pp. 582-584. http://archive.epo.org./epo.pubs/o1009/12_09/12_5829.pdf.

Kim, M.D., et al., "Hyperglycemia Control of the Nil Per Os Patient in the Intensive Care Unit: Introduction of a Simple Subcutaneous Insulin Algorithm", Nov. 2012, Journal of Diabetes Science and Technology, vol. 6, No. 6, pp. 1413-1419.

* cited by examiner

AIR DETECTION SYSTEM AND METHOD FOR DETECTING AIR IN A PUMP OF AN INFUSION SYSTEM

BACKGROUND OF THE INVENTION

Field of the Invention

The disclosure relates to systems and methods for detecting air in an infusion system.

Description of the Related Art

Existing systems and methods for detecting air in the line of an infusion device generally involve the use of ultrasonic sensors that detect the open circuit caused when air fills the volume between two sensor pairs. When the air sensor signal moves beyond a pre-defined air/fluid threshold, an alarm condition occurs and IV infusion is paused. Unfortunately, a variety of situations exist which either mask the presence of air, leading to false negatives, or generate false alarms. Fundamentally, this problem occurs because a single sensor with a univariate signal is applied to a relatively complex problem with multiple dimensions.

A system and method is needed which more accurately detects air in the line of an infusion device.

SUMMARY OF THE INVENTION

In one embodiment of the disclosure, a method for detecting air in a chamber of an infusion system is disclosed. In one step, a plunger is moved against a chamber containing fluid with an actuator device. In another step, a force acting on the plunger, as it moves against the chamber, is detected with a sensor. In an additional step, a measurement of the force acting on the plunger is electronically communicated from the sensor to a processor. In yet another step, a determination is made, with the processor, that the chamber contains air when: (1) a trigger event occurs in which a change in the force exceeds a threshold; and (2) subsequent to the trigger event a differential between a baseline average force acting on the plunger and a current average force acting on the plunger exceeds an expected force differential within a defined delay range.

In another embodiment of the disclosure, a method for detecting air in a chamber of an infusion system is disclosed. In one step, a plunger is moved against a chamber containing fluid with an actuator device. In another step, a force acting on the plunger, as it moves against the chamber, is detected with a sensor. In an additional step, a measurement of the force acting on the plunger is electronically communicated from the sensor to a processor. In yet another step, the processor is used to determine: (1) a baseline force profile; (2) a current force profile representing the current force acting on the plunger against the chamber; (3) a difference between the current force profile and the baseline force profile; and (4) that the chamber contains air when the calculated difference crosses a threshold.

In still another embodiment of the disclosure, a method for detecting air in a chamber of an infusion system is disclosed. In one step, a plunger is moved against a chamber containing fluid using an actuator device. In another step, a force acting on the plunger, as it moves against the chamber, is detected with a sensor. In yet another step, a measurement of the force acting on the plunger is electronically communicated from the sensor to a processor. In another step, the processor is used to: (1) preprocess a force profile detected by the sensor; (2) extract features from the force profile; and (3) classify the force profile as being an air force profile or a liquid force profile based on the extracted features of the force profile.

These and other features, aspects and advantages of the disclosure will become better understood with reference to the following drawings, description and claims.

DETAILED DESCRIPTION OF THE PREFERRED EMBODIMENT

Figure 1:
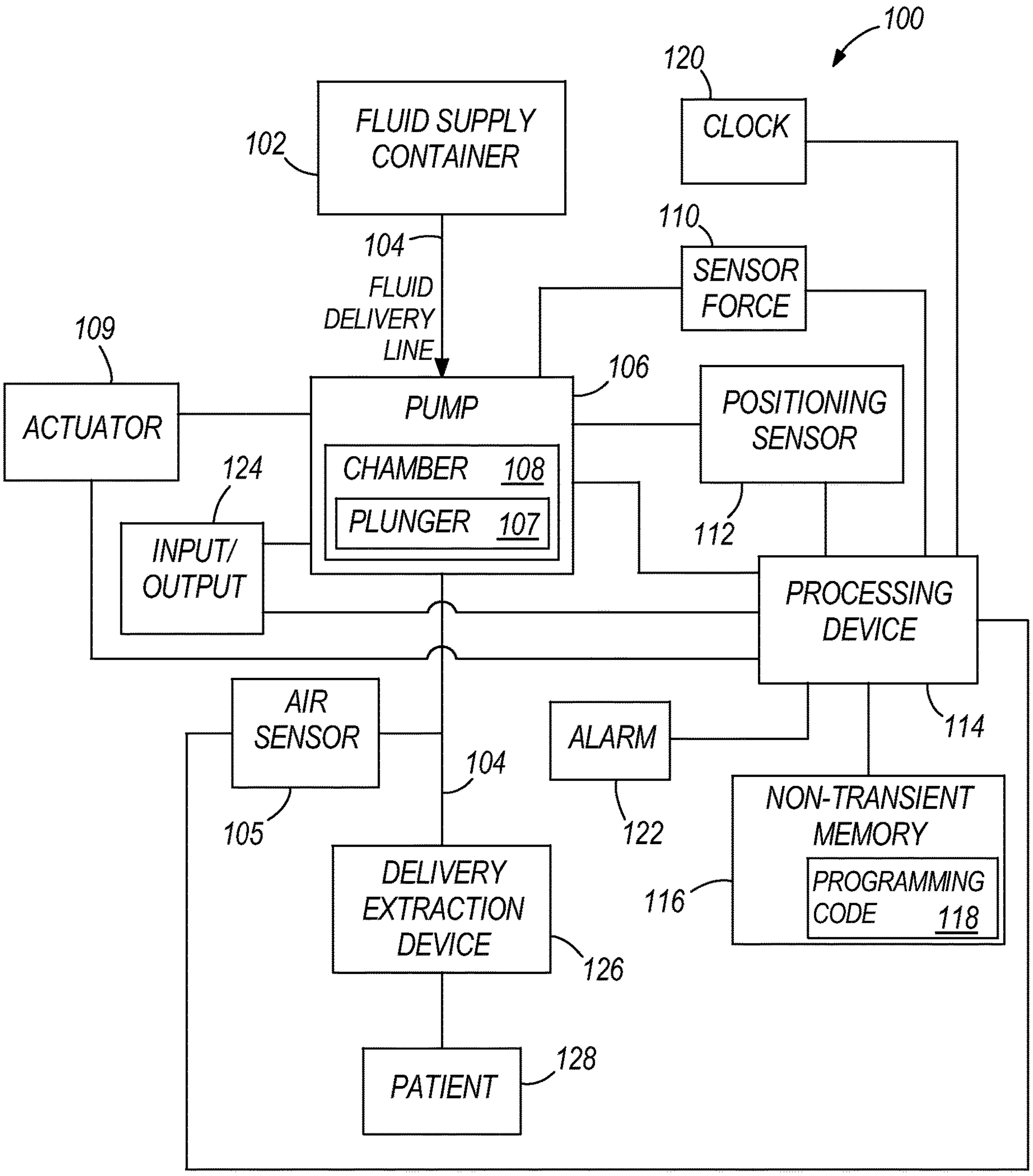
FIG. 1 illustrates a block diagram of a drug delivery infusion system under one embodiment of the disclosure.

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims. It is noted that the Figures are purely for illustrative purposes and are not to scale.

The instant disclosure provides methods and apparatus for determining whether air is present in an infusion system. Several types of pumps, such as Symbiq™, Plum™, and Gemstar™ pumps sold by Hospira, Inc., involve the use of a cassette with a chamber that is compressed by an actuated plunger to pump fluid at a controlled rate from the drug container to the patient. The chamber is surrounded by valves which open and close in a complimentary manner to ensure unidirectional flow. The measured force during a pumping cycle is directly related to the type of fluid in the chamber. Fluids are relatively incompressible and generate a higher and different force profile than air. Similarly, a combination of fluid and air in the chamber results in a hybrid shape profile which is indicative of the mixture percentages of both fluid and air. The instant disclosure discloses algorithms for utilizing the plunger force to detect the presence of air in the chamber to detect an air embolism prior to its infusion into a patient.

In one embodiment of the disclosure, an event detection algorithm is disclosed which determines a change from fluid to air in the pumping chamber on the basis of a change in the average force exerted against the plunger. The algorithm utilizes a derivative spike for event detection and a systematic reduction in the average force to confirm the nature of the change.

In another embodiment of the disclosure, a pattern recognition system/method is provided for recognizing fluid, air, or a mixture thereof in a pumping chamber. The system normalizes the force signal/profile acting on the plunger against the chamber to a baseline. The system then preprocesses the force signal/profile to smooth and re-samples the x-axis to a standard sampling interval with respect to plunger position. The system then extracts features such as the maximum absolute difference between the baseline and each subsequent force profile, or other types of features. The system then classifies the force profile as being air, fluid, or a combination thereof using linear discriminate analysis or another type of analysis system/method.

In still another embodiment of the disclosure, a varied pattern recognition system/method is provided for recognizing fluid, air, or a mixture thereof in a pumping chamber. The system, without normalizing to a baseline, preprocesses the force signal/profile acting on the plunger against the chamber by applying a low pass filter or by applying another type of preprocessing system/method. The system then extracts features from the entire force profile or a subset thereof such as the signal frequency content, the signal phase, the standard deviation or variance, the maximum, the range, the plunger position of critical points, the scores based on a principal component analysis, or extracts other types of features. The system then classifies the force profile as being air, fluid, or a combination thereof using linear discriminate analysis, k-nearestneighbor, support vector machines, or another type of analysis system/method.

One or more systems/methods of the disclosure include components that are optimized/customized according to a delivery rate of the fluid within the pumping chamber. Some of the existing algorithms fail to account for the profound impact of delivery rate on the observed plunger sensor force profile and the detection electronics. One or more systems/methods of the disclosure provide normalization or clustering states that reduce this impact and thereby improve sensitivity.

One or more systems/methods of the disclosure may be combined with any existing systems/methods for detecting air in an infusion system to improve the reliability of air detection systems. For instance, many current systems/methods use acoustic or ultrasonic sensors to detect the presence of air in tubing segments. However, these systems/methods often do not consider the possibility of an acoustic short circuit or a bubble that is stuck or repetitively passes in front of the sensor. Many systems/methods rely on a single air ultrasonic sensor with a fixed threshold which separates the air sensor signal into two regions representing air and fluid. When a voltage is measured that is within the air signal region, the volume of air represented by the signal is accumulated until an alarm condition is met. The disclosure allows for the combination of the output of a force sensor signal with one or more air sensors to improve the reliability of existing air detection systems/methods. In doing so, the disclosed system/method does not require additional hardware modifications but instead leverages the acquired force signal. Additionally, the disclosure does not necessarily require the replacement of existing software modules for air detection but adds an additional safety and/or reliability layer to improve the robustness of existing air detection systems and methods.

FIG. 1 illustrates a block diagram of a drug delivery infusion system 100 under one embodiment of the disclosure. The drug delivery infusion system 100 comprises: a fluid supply container 102; a fluid delivery line 104; an air sensor 105 connected to the fluid delivery line 104; a pump 106 comprising a plunger 107 moveably disposed against a chamber 108; an actuator device 109; a sensor 110; a positional sensor 112; a processing device 114; a non-transient memory 116 storing programming code 118; a clock 120; an alarm 122; an input/output device 124; and a delivery/extraction device 126. The drug delivery infusion system 100 may comprise a drug delivery infusion system such as the Plum A+™, Gemstar™, Symbig™, or other type of drug delivery infusion system. The fluid supply container 102 comprises a container for delivering fluid such as IV fluid or a drug to the patient 128 through the chamber 108 due to movement of the plunger 107 against the chamber 108. The fluid delivery line 104 comprises one or more tubes, connected between the fluid supply container 102, the pump 106, and the delivery/extraction device 126, for transporting fluid from the fluid supply container 102, through the pump 106, through the delivery/extraction device 126 to the patient 128. The fluid delivery line 104 may also be used to transport blood, extracted from the patient 128 using the delivery/extraction device 126, as a result of a pumping action of the pump 106. The pump 106 comprises a pump for pumping fluid from the supply container 102 or for pumping blood from the patient 128.

The pump 106 may comprise a plunger based pump, a peristaltic pump, or another type of pump. The chamber 108 comprises an inner cavity of the pump 106 into which fluid from the fluid supply container 102 is pumped into and through due to the moveably disposed plunger 107 moving against the chamber 108 as a result of the actuator device 109. The actuator device 109 may comprise a motor or another type of actuating device for moving the plunger 107 against the chamber 108. The sensor 110 is contained within the chamber 108 and detects the force acting on the plunger 107 as it moves against the chamber 108. The sensor 110 may comprise a force sensor signal comprising a pressure sensor, an elastic column, a strain gauge, or a piezoelectric crystal force transducer. The positional sensor 112 is used to determine a position of the plunger 107 against the chamber 108. The positional sensor 112 may comprise an encoder or may utilize the expected position based upon the commands sent to the actuator.

The processing device 114 is in electronic communication with the pump 106, the actuator device 109, the sensor 110, the positional sensor 112, the non-transient memory 116 storing the programming code 118, the clock 120, the alarm 122, and the input/output device 124. The processing device 114 comprises a processor for processing information received from the pump 106, the sensor 110, the positional sensor 112, and the clock 120, and for executing a software algorithm, contained in the programming code 118 stored in the non-transient memory 116, to determine if air, liquid (fluid), or a combination thereof is located in the chamber 108 of the pump 106. The non-transient memory 116 may be located within or outside of the processing device 114.

The clock 120 keeps time of activities of the drug delivery infusion system 100 including the plunger 107, the sensor 110, the positional sensor 112, and its other components. The alarm 122, when triggered by the processing device 114, is configured to notify the clinician as to the presence of air in the chamber 108, and to stop the pump 106 prior to an air embolism being delivered through the fluid delivery line 104 and the delivery/extraction device 126 to the patient 128. The input/output device 124 comprises a device which allows a clinician to input information, such as a user-inputted medication infusion program, to the processing device 114, and which also outputs information to the clinician. The delivery/extraction device 126 comprises a patient vascular access point device for delivering fluid from the fluid supply container 102 to the patient 128, or for extracting blood from the patient 128. The delivery/extraction device 126 may comprise a needle, a catheter, or another type of delivery/extraction device.

In one embodiment of the disclosure, the drug delivery infusion system 100 of FIG. 1 may determine when air is present in the chamber 108 by analyzing the force on the plunger 107 and the derivative of the force acting on the plunger 107 per delivered volume of the fluid or air exiting the chamber 108. This is because it has been discovered that when air reaches the chamber 108, the derivative force acting on the plunger 107 per the delivered volume of the fluid exiting the chamber 108 spikes in the downward direction and then returns to a baseline value, and that the average force on the plunger 107 then proceeds to drop slightly as the chamber 108 fills with air. To process this information, six data points per cycle of the plunger 107 may be gathered. In other embodiments, a varying number of data points per cycle of the plunger 107 may be gathered.

Figure 2:
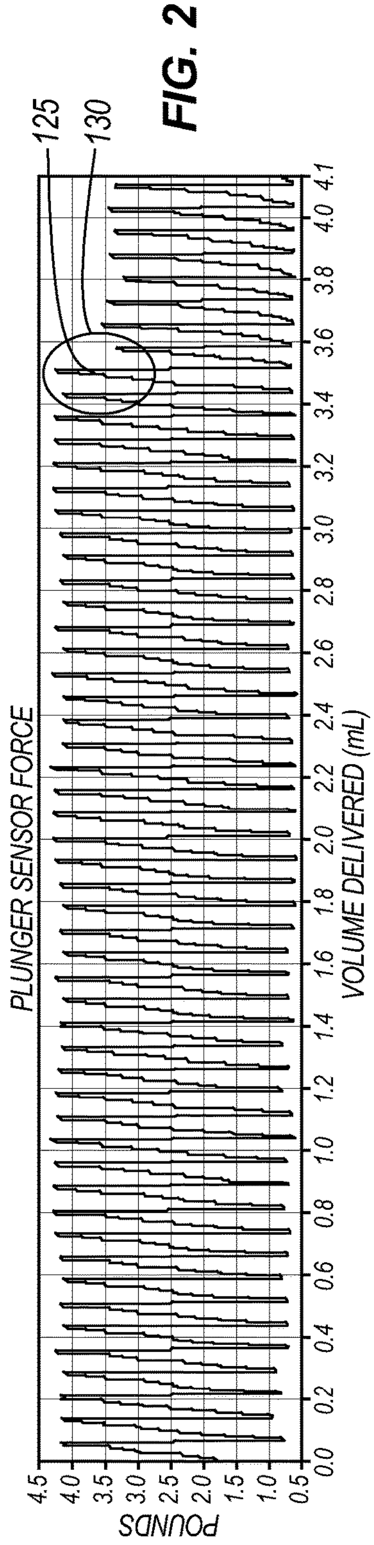
FIG. 2 illustrates a graph plotting a plunger sensor force curve per volume of fluid delivered.
Figure 3:
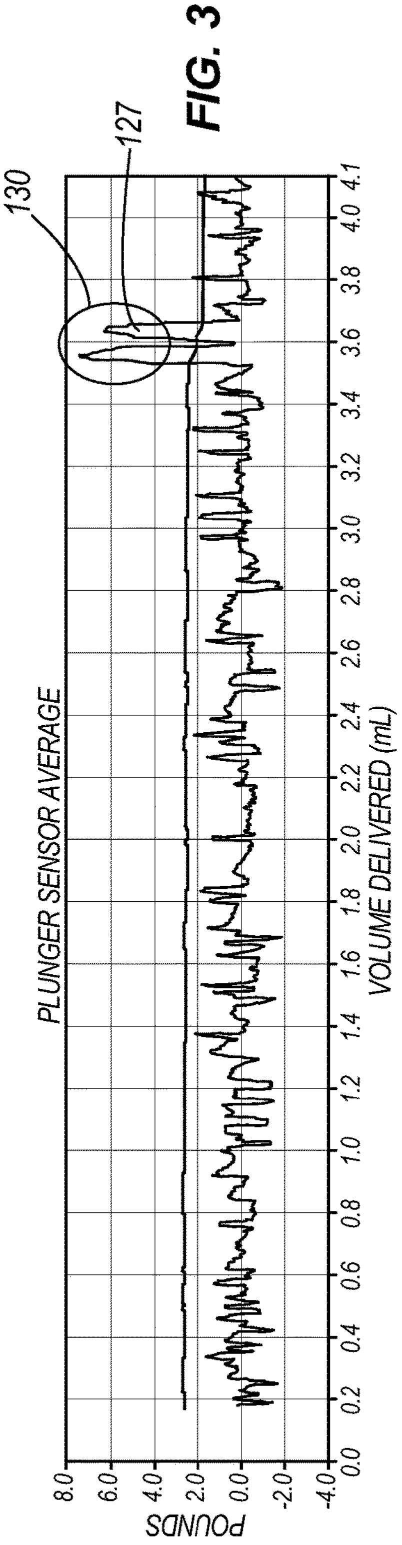
FIG. 3 illustrates a corresponding graph to FIG. 2 plotting a plunger sensor force negative derivative curve per volume of fluid delivered.
Figure 4:
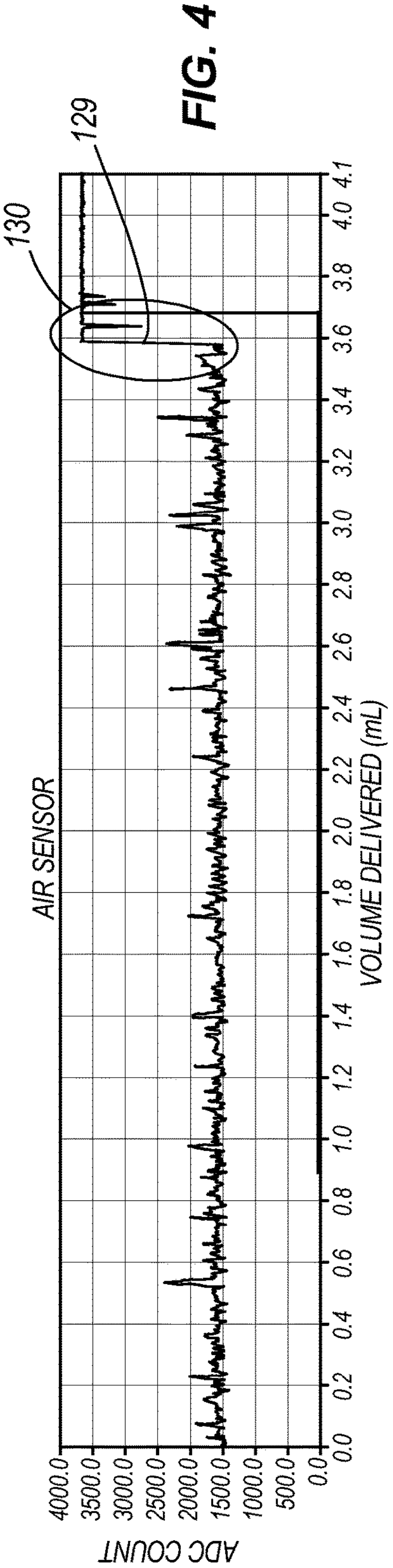
FIG. 4 illustrates a corresponding graph to FIGS. 2 and 3 plotting an in-line sensor ADC curve per volume of fluid delivered.

Corresponding FIGS. 2-4 illustrate typical data for one embodiment of a single iteration and end-of-bag event in which air is discovered in the chamber of FIG. 1. FIG. 2 illustrates a graph plotting a plunger sensor force curve 125 per volume of fluid delivered. The Y-axis represents pounds of force on the plunger detected by a plunger force sensor and the X-axis represents volume in milliliters of the fluid delivered from the chamber. FIG. 3 illustrates a corresponding graph to FIG. 2 plotting a plunger sensor force negative derivative curve 127 per volume of fluid delivered. The Y-axis represents a derivative of the average force on the plunger of FIG. 2 in pounds per unit volume and the X-axis represents volume in milliliters of the fluid delivered from the chamber. FIG. 4 illustrates a corresponding graph to FIGS. 2 and 3 plotting an in-line air sensor ADC curve 129 per volume of fluid delivered. The Y-axis represents an ADC count (also referred to as Analog-to-Digital-Count) of the fluid in-line as detected by an air sensor and the X-axis represents volume in milliliters of the fluid delivered from the chamber. As illustrated by FIG. 3, the transition from fluid to air occurs at the point in volume where the derivative of the force on the plunger spikes at location 130. As illustrated by FIG. 2, the force on the plunger drops at this same location 130. As illustrated by FIG. 4, the ADC count dramatically increases at this same location 130.

Figure 5:
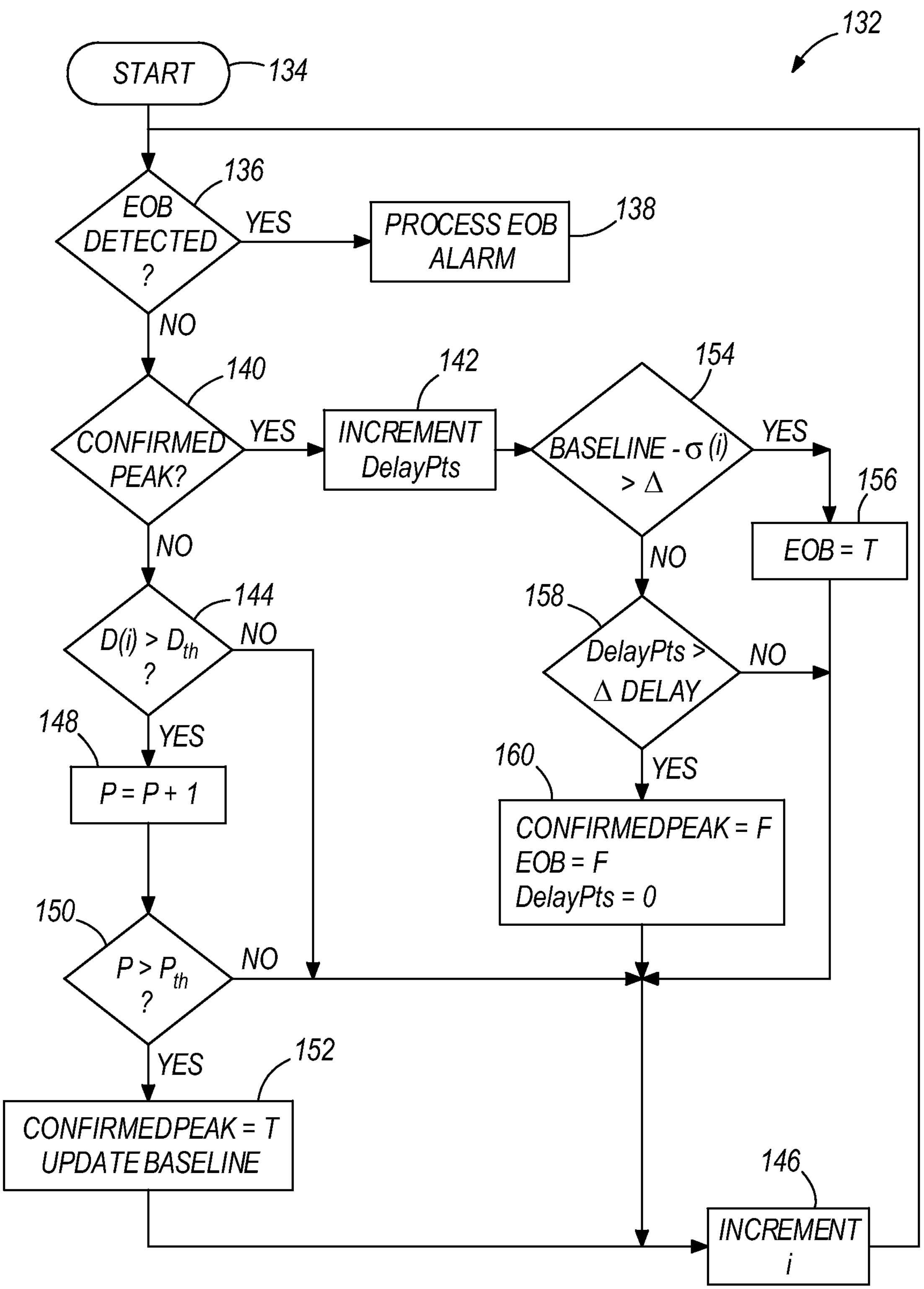
FIG. 5 illustrates one embodiment of a method, comprising a continuous flow chart, under the disclosure for determining whether air is contained in a chamber of a pump.

FIG. 5 illustrates one embodiment of a method 132, comprising a continuous flow chart, under the disclosure for determining whether air is contained in a chamber of a pump. The method 132 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 132, and the alarm being turned on if the processor determines that air is contained in the chamber which may trigger the pump being shut down. Moreover, the method 132 may utilize the clock of the drug delivery infusion system 100 of FIG. 1 to keep time of activities of the plunger or the sensor, and may use the positional sensor to determine a position of the plunger. In other embodiments, the method 132 may utilize varying components to implement the method.

In step 134, the method starts. After step 134, in step 136 a determination is made as to whether the end-of-bag (EOB), or equivalent situation in which the chamber contains air, has been detected. If the answer to the determination in step 136 is 'yes' and the end of the bag has been detected, the method proceeds to step 138 and an end-of-bag alarm is turned on to indicate that air is in the chamber. This end-of-bag (EOB) event may pause the pump infusion or be used by another algorithm to qualify an air-in-line alarm. If the answer to the determination in step 136 is 'no' and the end of the bag has not been detected, the method proceeds to step 140 in which a determination is made as to whether there is a previously confirmed peak. If the answer to the determination in step 140 is 'yes' and there is a confirmed peak, the method proceeds to step 142 which is discussed more thoroughly below. If the answer to the determination in step 140 is 'no' and there is not a previously confirmed peak, the method proceeds to step 144 in which a determination is made as to whether a trigger event has occurred in which the current negative derivative (of the average force) D(i) of the force of the plunger per delivered volume of the fluid exiting the chamber exceeds a derivative threshold Dih which indicates the beginning of a possible end-of-bag (EOB) event signifying that air may have entered the chamber. It should be noted that variable i is initially set to 1. The derivative threshold Dih is flow dependent. The derivative threshold Dih may be set to 1.5 for a flow rate of the fluid below 200 milliliters per hour and to 3.0 for a flow rate of the fluid above 200 milliliters per hour. In other embodiments, the derivative threshold Dih may be varied as a direct function of flow rate.

If the answer to the determination in step 144 is 'no,' the method proceeds to step 146, increments variable i using the equation i=i+1, and then proceeds back to and repeats step 136. If the answer to the determination in step 144 is 'yes,' the method proceeds to step 148 and increments variable P applying using the equation P=P+1. It should be noted that variable P is initially set to 0. After step 148, the method proceeds to step 150 in which a determination is made as to whether variable P is greater than the consecutive point threshold Pih. In one embodiment, the consecutive point threshold Pih is set to 1. In other embodiments, the consecutive point threshold Pih may be varied. The consecutive point threshold Pih represents one less than the number of consecutive points P that the current negative derivative (average) D(i) of the force of the plunger versus volume of the fluid delivered must exceed a derivative threshold D1*h* in order to indicate a possible end-of-bag (EOB) event signifying that air may be in the chamber. If the answer to the determination in step 150 is 'no,' the method proceeds to step 146, increments i applying the equation i=i+1, and then proceeds back to and repeats step 136. If the answer to the determination in step 150 is 'yes,' the method proceeds to step 152 in which the peak is confirmed, and a baseline B is taken.

The baseline B represents the average force during infusion when the chamber is filled with fluid. In one embodiment, the baseline B comprises the average force acting on the plunger over a defined baseline range occurring up to the trigger event. In one embodiment, the defined baseline range comprises the immediately previous 100 micro liters of average force data on the plunger taken immediately previous and up to the trigger event. In one embodiment, the baseline range may comprise multiple cycles of average force data. In other embodiments, the baseline range may vary. The trigger event comprises the point at which the negative derivative force D(i) acting on the plunger per the delivered volume of the fluid exiting the chamber first exceeds the derivative threshold D1*h* so long as subsequently the number of consecutive measured points P of the cycle of the plunger from the trigger event, in which the negative derivative force D(i) acting on the plunger per the delivered volume of the fluid exiting the chamber continues to exceed the derivative threshold D1*h*, exceeds the consecutive point threshold Pih. In other embodiments, the trigger event may vary. After step 152, the method proceeds to step 146, increments variable i using the equation i=i+1, and then proceeds back to and repeats step 136.

As referred to earlier, if the answer to the determination in step 140 is 'yes' and there is a confirmed peak, the method proceeds to step 142 and increments the delay points DP using the equation delay points=delay points+1. The delay points are initially set to zero. The delay points represent the number of data points taken of the cycle of the plunger since the confirmed peak. After step 142, the method proceeds to step 154 and makes a determination as to whether the differential between the baseline B and the current average force σ(i) is greater than the expected force differential Δ. The current average force σ(i) comprises the current average force on the plunger taken over a certain number of points of the cycle up to the current point of the plunger. In one embodiment, the current average force on the plunger may be calculated based on two cycles of the plunger immediately preceding and up to the current point of the plunger. In other embodiments, the current average force on the plunger may be taken over a varied range. In one embodiment, the expected force differential Δ comprises 0.15 pounds of force. In other embodiments, the expected force differential Δ may vary.

If the answer to the determination in step 154 is 'yes,' the method proceeds to step 156, confirms that an end-of-bag (EOB) or equivalent event has occurred, and proceeds through steps 146, 136, and 138 to turn on the end-of-bag alarm to indicate that air is in the chamber. This end-of-bag (EOB) event may turn off the pump. If the answer to the determination in step 154 is 'no,' the method proceeds to step 158 and makes a determination as to whether the delay points DP is greater than a Δ delay point threshold. The Δ delay point threshold comprises a defined delay range, starting from the point of the trigger event, over which the differential between the baseline B and the current average force σ(i) must exceed the expected force differential Δ in order to determine that an end-of-bag (EOB) event has occurred. In one embodiment, the Δ delay point threshold comprises 200 micro liters of delivered fluid. In other embodiments, the Δ delay point threshold may vary.

If the answer to the determination in step 158 is 'no,' the method proceeds to step 146, increments variable i using the equation i=i+1, and then proceeds back to and repeats step 136. If the answer to the determination in step 158 is 'yes,' the method proceeds to step 160, determines that there is no confirmed peak, determines that there is no end-of-bag (EOB) event, resets the delay points DP to zero, proceeds to step 146, increments variable i using the equation i=i+1, and then proceeds back to and repeats step 136. In other embodiments, one or more steps of the method 132 may be modified, not followed, or one or more additional steps may be added. Moreover, any of the variables of method 132 may be either user set, using an input device, or preset into the processor.

Figure 6:
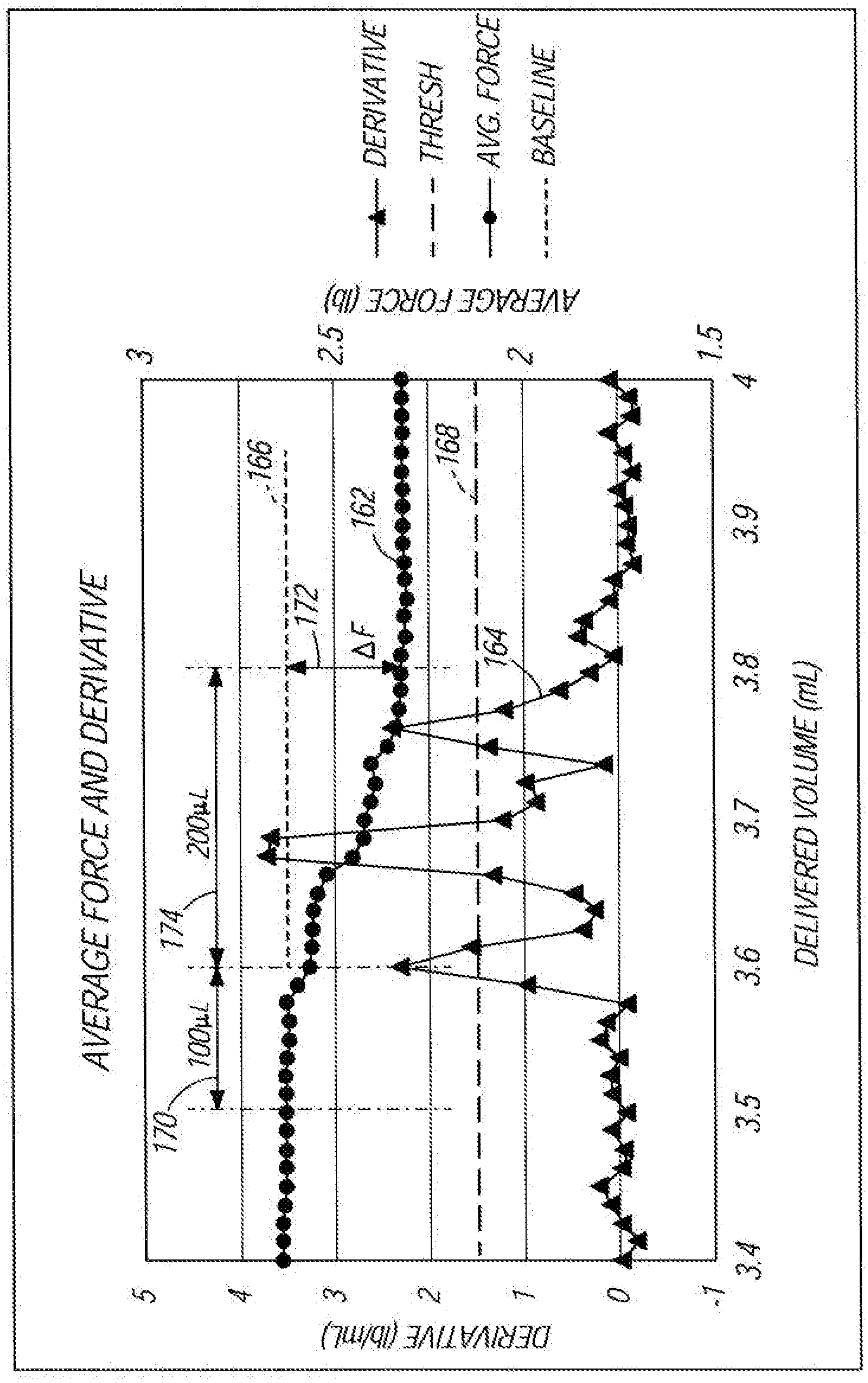
FIG. 6 illustrates a graph plotting, for a representative example, an average plunger sensor force curve, a plunger sensor force derivative curve, a baseline, a derivative threshold, a defined baseline range, an expected force differential Li, and a/ ∷,. delay point threshold.

FIG. 6 illustrates a graph plotting, for a representative example, an average plunger sensor force curve 162, a plunger sensor force (negative) derivative curve 164, a baseline 166, a derivative threshold 168, a defined baseline range 170, an expected force differential σ172, and a Δ delay point threshold 174. The right-most Y-axis represents average pounds of force on the plunger detected by a plunger force sensor, the left-most Y-axis represents a derivative (average) of the force on the plunger of FIG. 2 in pounds per milliliter, and the X-axis represents volume in milliliters of the fluid delivered from the chamber. The average plunger sensor force curve 162 comprises the average force delivered with each circle representing a measured point of the cycle of the plunger with measured data point 1 being the first circle shown in the graph. The plunger sensor force derivative curve 164 comprises the derivative force per volume delivered with each triangle representing a measured point of the cycle of the plunger with measured derivative data point 1 being the first derivative triangle shown in the graph. The baseline 166 comprises a horizontal line 166. The derivative threshold 168 comprises a horizontal line. The defined baseline range 170 comprises a horizontal distance which in this example is 100 micro liters. The expected force differential Δ172 comprises a vertical distance. The Δ delay point threshold 174 comprises a horizontal distance which in this example is 200 micro liters.

The method of FIG. 5 may be applied to the example of FIG. 6 as follows to determine if air is contained in the chamber. In step 134, the method starts. The method then proceeds to step 136 and a determination is made that the end-of-bag (EOB) has not been detected for measured point i=1. The method then proceeds to step 140 and a determination is made that there is not a confirmed peak for measured point i=1. The method then proceeds to step 144 and a determination is made that the derivative for measured point i=1 has not exceeded the derivative threshold. The method then proceeds to step 146, increments variable i, and the method then repeats step 136. The method continues to loop in the same manner until a determination is made in step 144 that the derivative for measured point i=17 exceeds the derivative threshold. The method then proceeds to step 148 and increments variable P from 0 to 1. The method then proceeds to step 150 and determines that variable P which currently equals 1 is not greater than the consecutive point threshold Pih of 1. The method then proceeds to step 146, increments i to 18, and repeats steps 136, 140, and 144. In step 144, a determination in is made that the derivative of measured point i=18 exceeds the derivative threshold. The method then proceeds to step 148 and increments variable P from 1 to 2. The method then proceeds to step 150 and determines that variable P which currently equals 2 is greater than the consecutive point threshold Pih of 1. The method then proceeds to step 152, confirms a peak, and takes a baseline B for the baseline range of 100 micro liters of average force data immediately prior to and up to measured point i=17 which is the trigger event. The method then proceeds to step 146, increments variable i to 19 and proceeds back to and repeats step 136.

In step 136, a determination is made that the end-of-bag (EOB) has not been detected for measured point 19. The method then proceeds to step 140 and determines that there is a confirmed peak for measured point i=19. The method then proceeds to step 142 and increments the delay points DP to 1. The method then proceeds to step 154 and determines that the differential between the baseline B and the current average force σ(i) for measured point i=19 is not greater than the expected force differential Δ. The method then proceeds to step 158 and determines that the delay points DP of 1 is not greater than the Δ delay point threshold comprising the number of measured points in the cycle of the plunger, starting from the trigger event, within 200 micro liters of fluid delivered from the chamber. The method then proceeds to step 146, increments i and proceeds back to and repeats step 136. The method continues to loop through steps 136, 140, 142, and 154 until it is determined in step 154 that the differential between the baseline B and the current average force σ(i) for measured point i=23 is greater than the expected force differential Δ. The method then proceeds to step 156, confirms that an end-of-bag (EOB) event has occurred, and proceeds through steps 146, 136, and 138 to turn on the end-of-bag alarm to indicate that air is in the chamber. The end-of-bag alarm being turned on may further comprise pausing the infusion.

The method of FIG. 5 was implemented to analyze 472 data sets for a variety of flow rates. The testing resulted in no false positive determinations of air being in the chamber and only one occurrence of a false negative which only equated to 0.2% of the sets resulting in an incorrect result.

Figure 7:
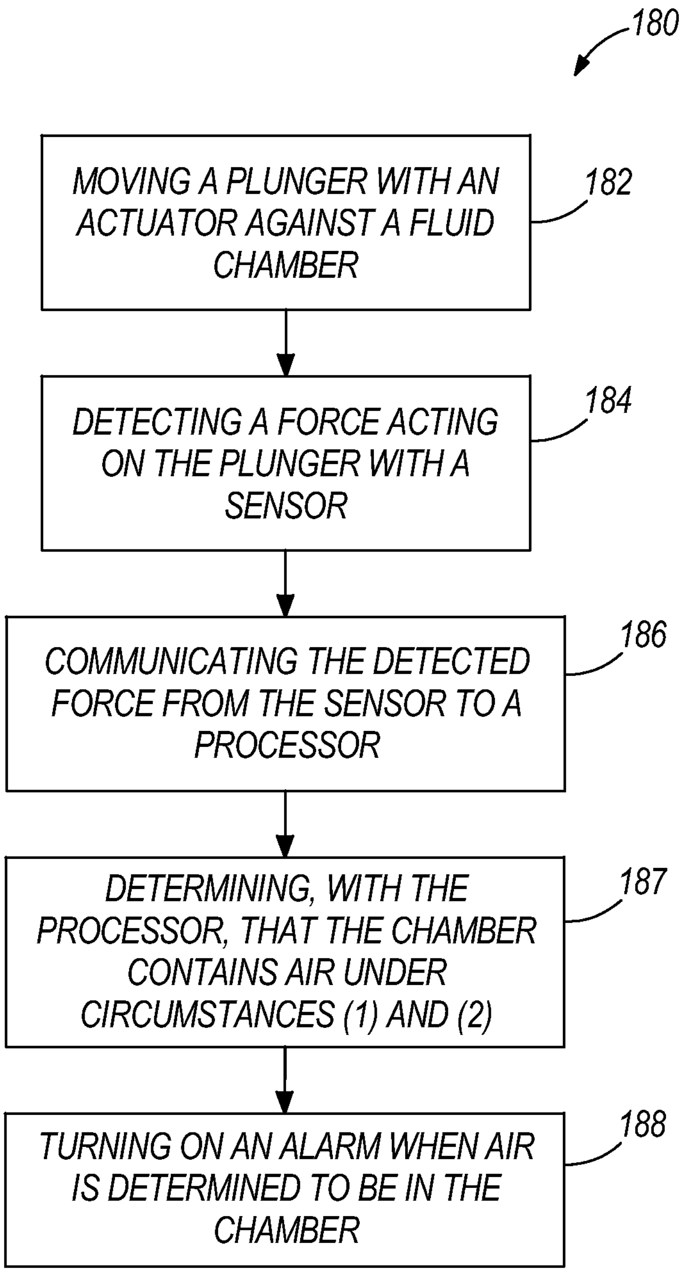
FIG. 7 illustrates a flowchart for one embodiment of a method for detecting air in a chamber of an infusion system.

FIG. 7 illustrates a flowchart for one embodiment of a method 180 for detecting air in a chamber of an infusion system. The method 180 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 180, and the alarm being turned on if the processor determines that air is contained in the chamber which may trigger the pump being shut down. Moreover, the method 180 may utilize the clock of the drug delivery infusion system 100 of FIG. 1 to keep time of activities of the plunger or the sensor, and may use the positional sensor to determine a position of the plunger, with each being in electronic communication with the processor. In other embodiments, the method 180 may utilize varying components to implement the method.

In step 182 a plunger is moved with an actuator device against a chamber containing fluid. In step 184 a force acting on the plunger is detected with a sensor as the plunger moves against the chamber. In step 186 a measurement of the force is electronically communicated from the sensor to a processor. In step 187 a determination is made, with the processor, that the chamber contains air when: (1) a trigger event occurs in which a change in force acting on the plunger per delivered volume of the fluid exiting the chamber exceeds a threshold; and (2) subsequent to the trigger event a differential between a baseline average force acting on the plunger and a current average force acting on the plunger exceeds an expected force differential within a defined delay range. In step 188 the processor turns on an alarm when the processor determines that the chamber contains the air. Step 188 may further comprise shutting down the pump when the alarm is turned on.

In one embodiment of step 187 step (1), which must occur for the processor to determine that the chamber contains air, may further comprise for a consecutive number of measured points of a cycle of the plunger from the trigger event the derivative force acting on the plunger per the delivered volume of the fluid exiting the chamber continuing to exceed the derivative threshold for more than a threshold number of the measured points of the cycle of the plunger against the chamber. In one embodiment of step 187 the baseline average force of step (2) may comprise the average force acting on the plunger over a defined baseline range occurring up to the trigger event. The baseline average force may further represent the chamber being filled with the fluid. In other embodiments, any of the steps of method 180 may be altered, not followed, or additional steps may be added.

In another embodiment of the disclosure, the drug delivery infusion system 100 of FIG. 1 may determine when air is present in the chamber 108 by analyzing a shape of the force profile on the plunger 107 and determining that air is contained in the chamber 108 when the shape of the force profile on the plunger 107 changes significantly from a baseline shape of a force profile representing liquid being in the chamber 108. This is because it has been discovered that when air reaches the chamber 108, the shape of the force profile on the plunger 107 during a stroke or cycle of the plunger 107 changes in a consistent manner when and after the transition is made from fluid being in the chamber 108 to air being in the chamber 108. The shape of the force profile on the plunger 107 can be used as for detecting air-in-line by discriminating the force profile shapes associated with air and fluid. The characteristics of the shape of the force profile depend on the delivery rate of the fluid being delivered from the chamber 108 with some variability related to mechanism, set, fluid type, and distal and proximal pressure.

Figure 8:
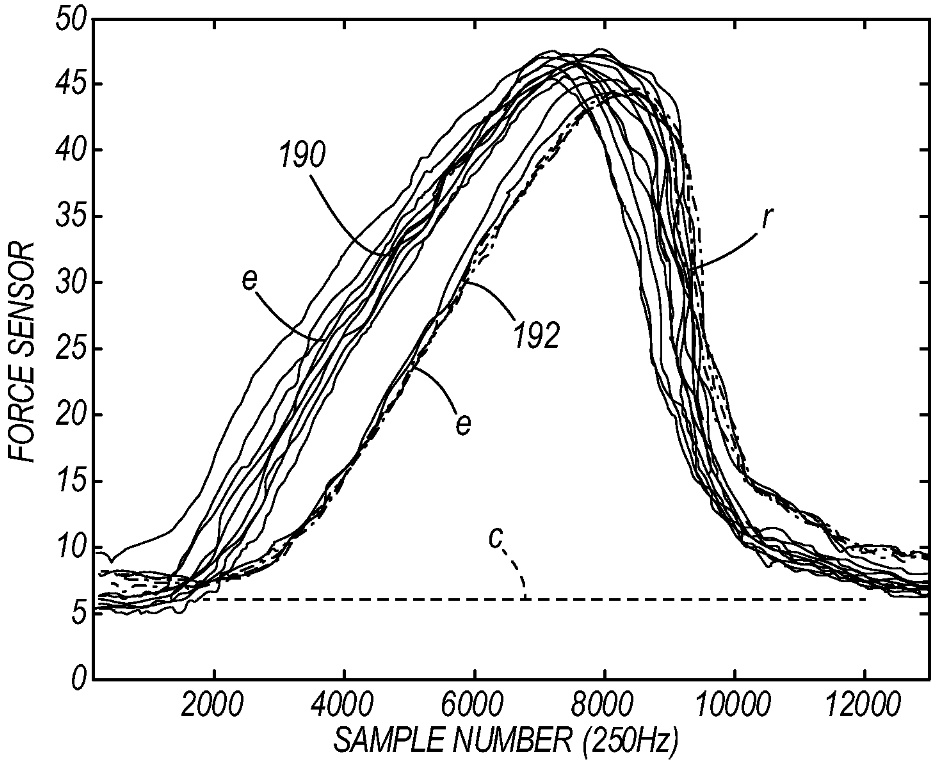
FIG. 8 illustrates a representative graph for one embodiment plotting a force sensor profile for a liquid curve and an air curve.

FIG. 8 illustrates a representative graph for one embodiment plotting a force sensor profile for a liquid curve 190 and an air curve 192. The Y-axis represents pounds of force on the plunger detected by a plunger force sensor and the X-axis represents a sample number collected at a rate of 250 Hz. Liquid curve 190 represents liquid being disposed in the chamber. Air curve 192 represents air being disposed in the chamber. As shown, the liquid curve 190 has substantially higher forces on the plunger than the air curve 192 during the expansion portion e of each cycle c of the plunger, while the difference between the curves 190 and 192 during the retraction phase r is significantly less.

Figure 9:
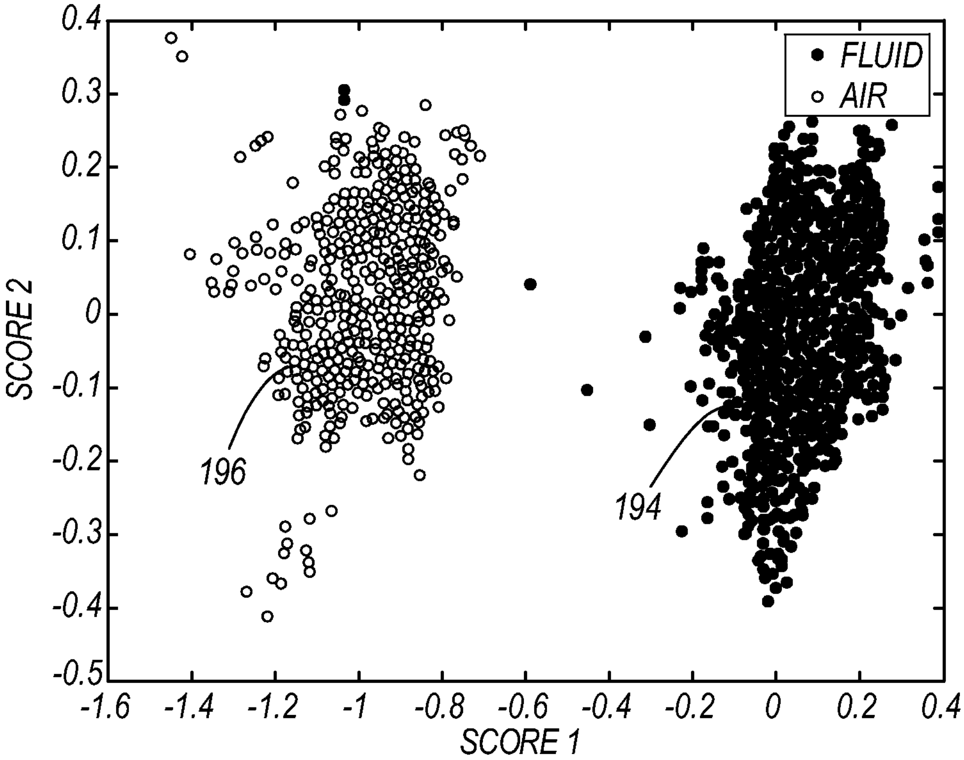
FIG. 9 illustrates a representative graph for one embodiment of a principal component analysis (PCA) which was done on a plunger force profile.

FIG. 9 illustrates a representative graph for one embodiment of a principal component analysis (PCA) which was done on a plunger force profile with points 194 representing liquid being disposed in the chamber and points 196 representing air being disposed in the chamber. The X-axis represents a first score and the Y-axis represents a second score. As shown, the points 194 representing liquid being disposed in the chamber have a higher first score than the points 196 representing air being disposed in the chamber.

Figure 10:
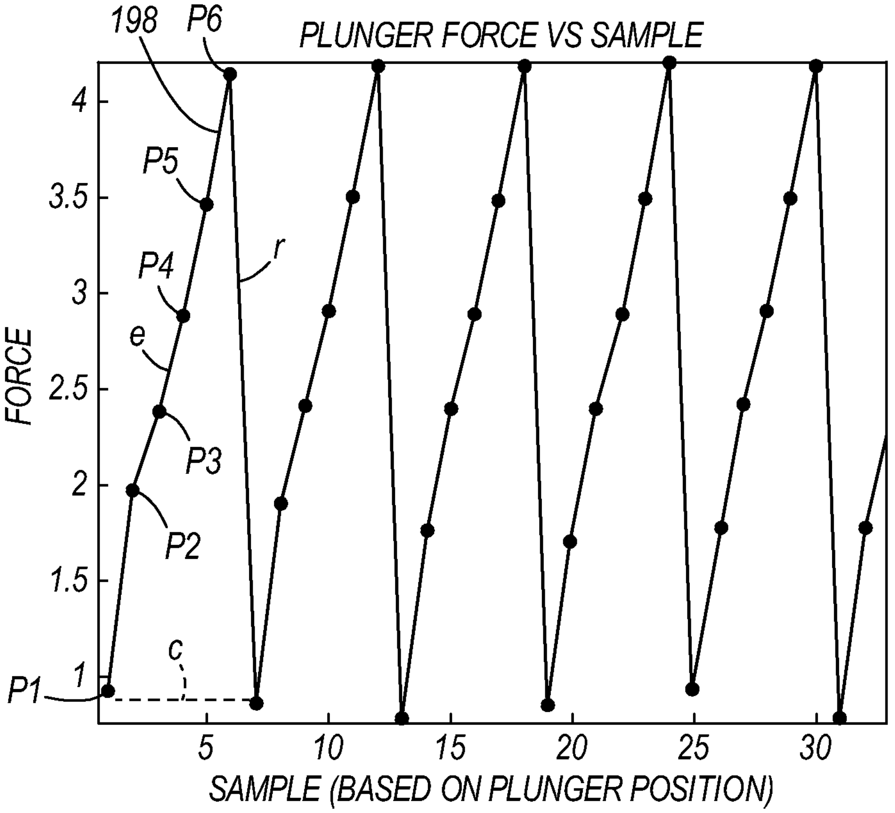
FIG. 10 illustrates a representative graph for one embodiment plotting a plunger force profile.

FIG. 10 illustrates a representative graph for one embodiment plotting a plunger force profile 198. The Y-axis represents pounds of force on the plunger detected by a plunger force sensor and the X-axis represents sample number for each cycle c of the plunger. As shown, six points p1-p6, comprising a 6 point vector pattern, are sampled at specific plunger positions during the expansion portion e of each cycle (or stroke) c of the plunger. No points are sampled during the retraction portion r of each cycle c of the plunger. This force sampling of each cycle may be used to determine whether air or liquid is contained in the chamber based on the shape of the measured force profile. The determination may be made using principle component analysis (PCA) to determine the correlation between the pattern variance of fluid versus air being in the chamber. Pre-processing may be applied to normalize the patterns across sets/needle heights and varying mechanisms. Separate analysis is performed for each separate fluid infusion rate or ranges of infusion rates. In other embodiments, a varying number of points per cycle of the plunger may be utilized, and the determination may be made using varying types of analysis.

Figure 11:
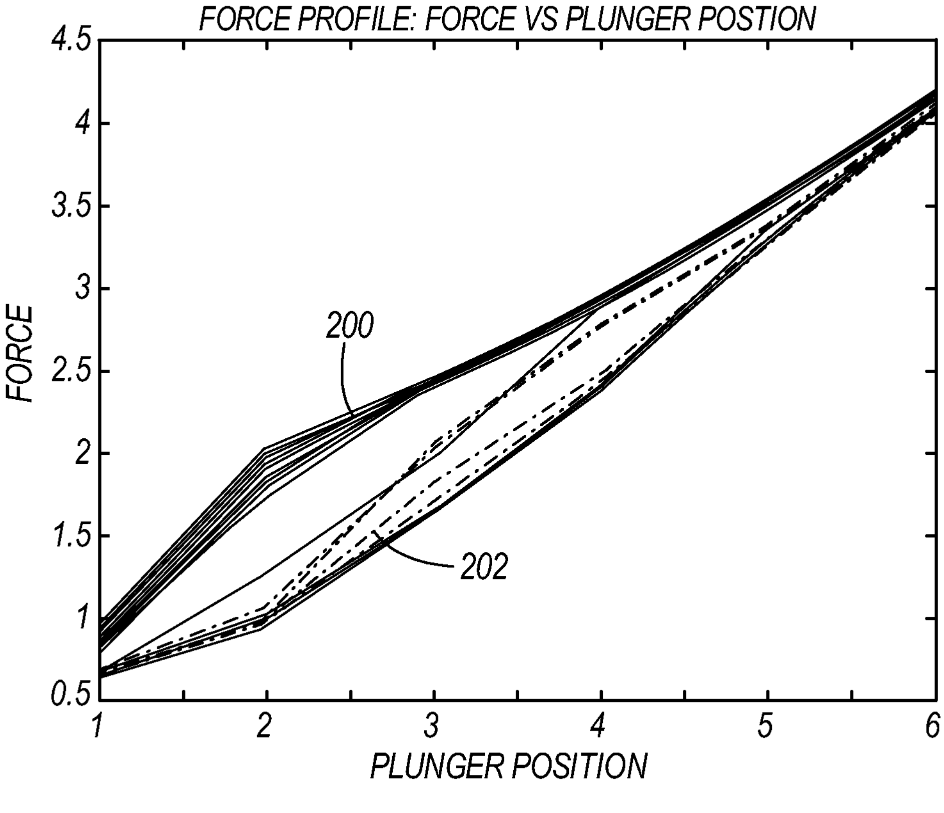
FIG. 11 illustrates a representative graph for one embodiment plotting a liquid plunger force curve and an air plunger force curve.

FIG. 11 illustrates a representative graph for one embodiment plotting a liquid plunger force curve 200 and an air plunger force curve 202. The Y-axis represents pounds of force on the plunger detected by a plunger force sensor and the X-axis represents a sample number of a cycle of the plunger. Liquid plunger force curve 200 represents liquid being disposed in the chamber. Air plunger force curve 202 represents air being disposed in the chamber. As shown, the liquid plunger force curve 200 has substantially higher forces on the plunger than the air plunger force curve 202.

Figure 12:
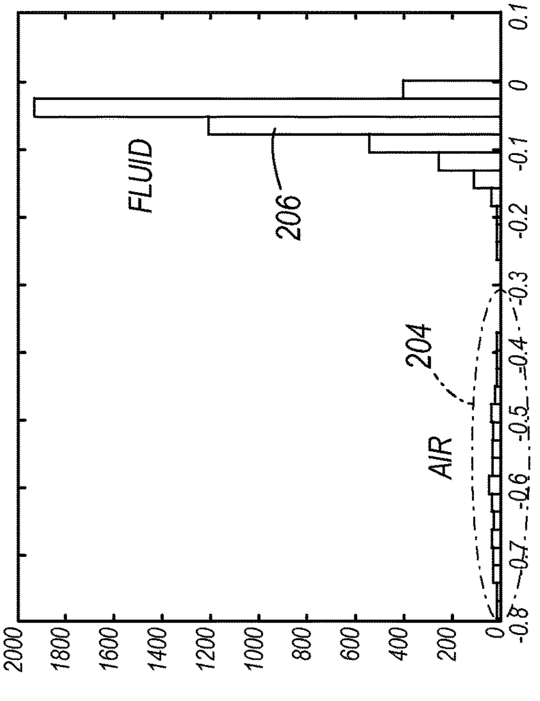
FIG. 12 illustrates a representative graph for one embodiment plotting, at an infusion rate of 20 ml/hour, the distribution of the maximum absolute difference between a reference plunger force profile and subsequent profiles comprising an air curve and a liquid curve.
Figure 13:
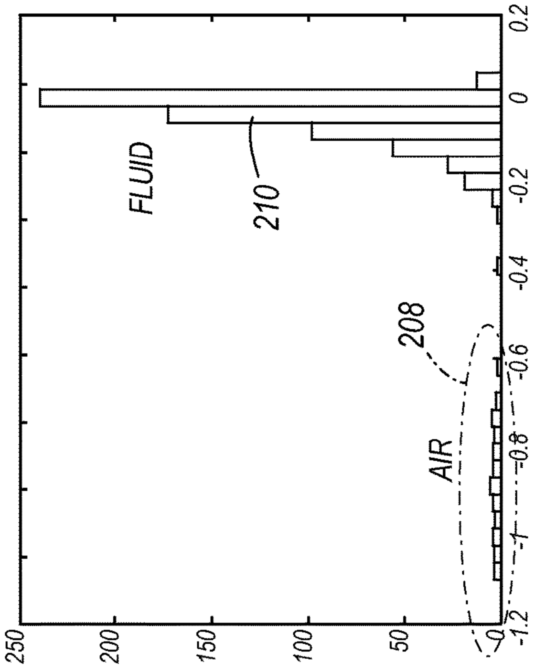
FIG. 13 illustrates a representative graph for one embodiment plotting, at an infusion rate of 550 ml/hour the distribution of the maximum absolute difference between a reference plunger force profile and subsequent profiles comprising an air curve and a liquid curve.

FIG. 12 illustrates a representative graph for one embodiment plotting, at an infusion rate of 20 ml/hr, the distribution of the maximum absolute difference between a reference plunger force profile and subsequent profiles comprising an air curve 204 and a liquid curve 206. The Y-axis represents the number of profiles and the X-axis represents the difference associated with the point of the maximum absolute difference between the measured force profile and the baseline profile. Air curve 204 represents air being disposed in the chamber and liquid curve 206 represents liquid being disposed in the chamber. As shown, the liquid curve 206 has a substantially lower difference from the (liquid) baseline than the air curve 204. FIG. 13 illustrates a representative graph for one embodiment plotting, at an infusion rate of 550 ml/hr, the distribution of the maximum absolute difference between a reference plunger force profile and subsequent profiles comprising an air curve 208 and a liquid curve 210. The Y-axis represents the number of profiles and the X-axis represents the difference associated with the point of the maximum absolute difference between the measured force profile and the baseline profile. Air curve 208 represents air being disposed in the chamber and liquid curve 210 represents liquid being disposed in the chamber. As shown, the liquid curve 210 has a substantially lower difference from the (liquid) than the air curve 208. FIGS. 12 and 13 demonstrate a significant difference between air and fluid across varying infusion rates after the maximum difference calculation is applied for feature extraction.

Figure 14:
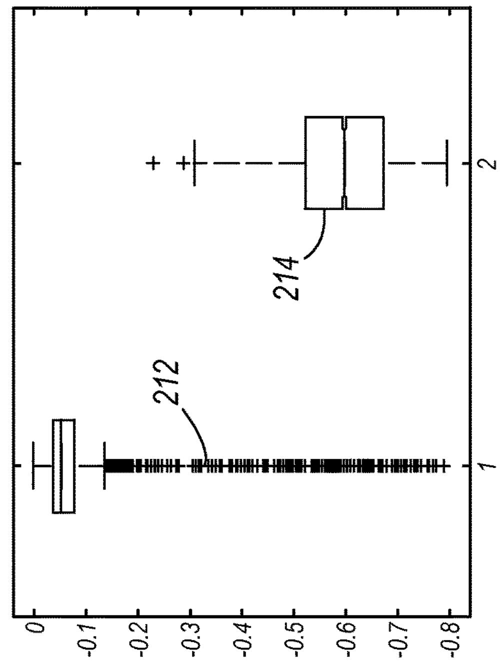
FIG. 14 illustrates a representative graph for one embodiment plotting, at an infusion rate of 20 ml/hr, an air plot and a liquid plot.

FIG. 14 illustrates a representative graph for one embodiment plotting, at an infusion rate of 20 ml/hr air depiction 212 and liquid depiction 214. The Y axis represents the difference between the observed force and the and the X axis represents two groups: (1) the group of differences associated with liquid in the plunger chamber; and (2) the difference with air in the plunger chamber Air depiction 212 represents air being disposed in the chamber and liquid depiction 214 represents liquid being disposed in the chamber. As shown, the air depiction 212 has a substantially lower (more negative) difference from the liquid baseline while the fluid 212 has a difference that is close to zero from the liquid baseline. The separation between the two groups provides the basis for a method for discriminating force measurements associated with air from those associated with fluid.

An algorithm has been discovered that normalizes a force shape profile of a plunger by determining a baseline force profile specific to each infusion program, and by using one generic feature, independent of the infusion program/rate, to assess whether air is contained in the chamber. To implement the algorithm, each force shape profile of the plunger is compared to a baseline force profile, a point-by-point difference between the force shape profile and the baseline force profile is determined, and when the minimum (most negative) difference between the force shape profile and the baseline force profile drops below a threshold a determination is made that the chamber contains air. The baseline force profile may represent liquid being in the chamber. In other embodiments, varying algorithms may be implemented to determine when air is contained in the chamber based on the force shape profile of the plunger.

Figure 15:
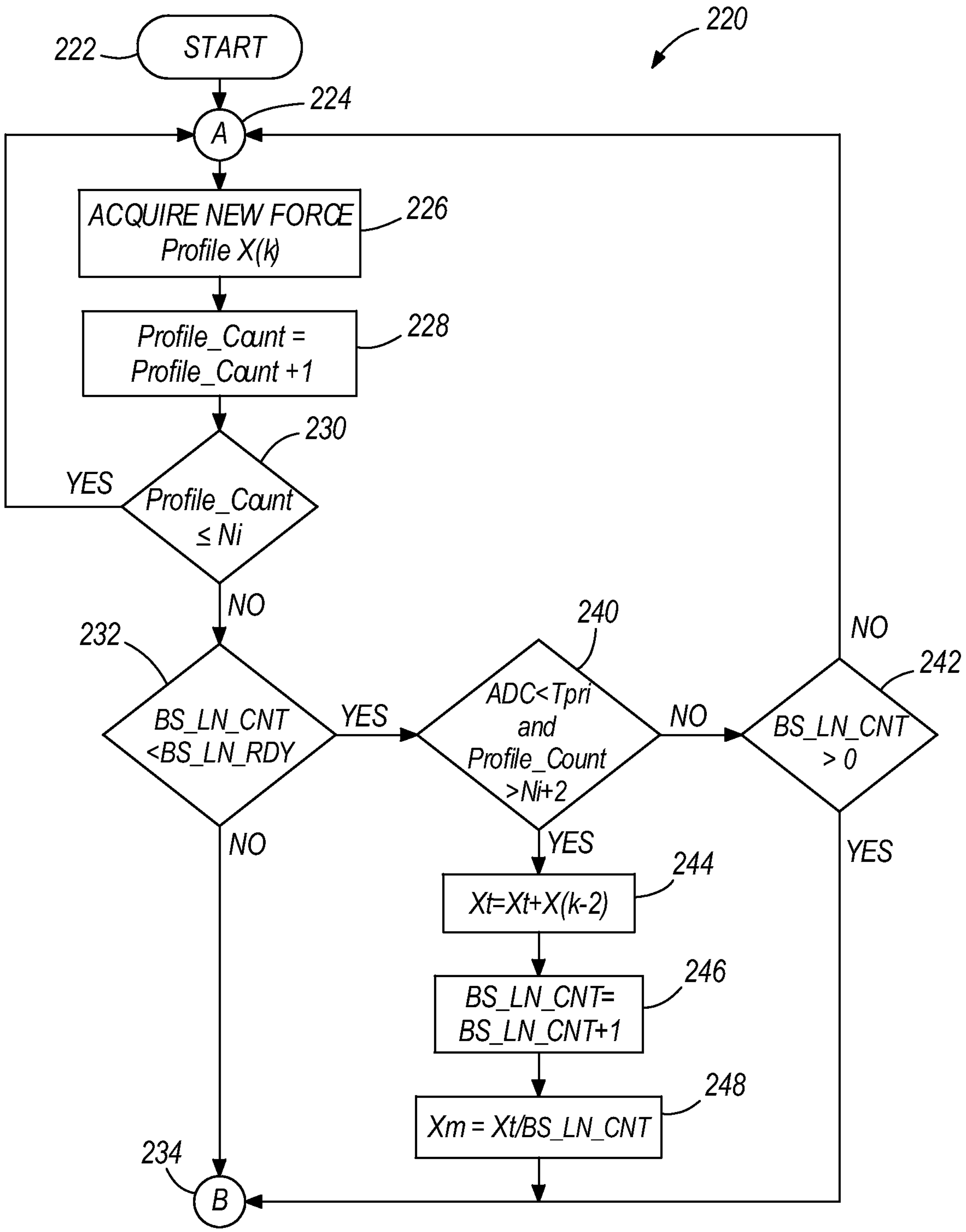
FIG. 15 illustrates one embodiment of a method, comprising a continuous flow chart, under the disclosure for determining whether air is contained in a chamber of a pump.
Figure 16:
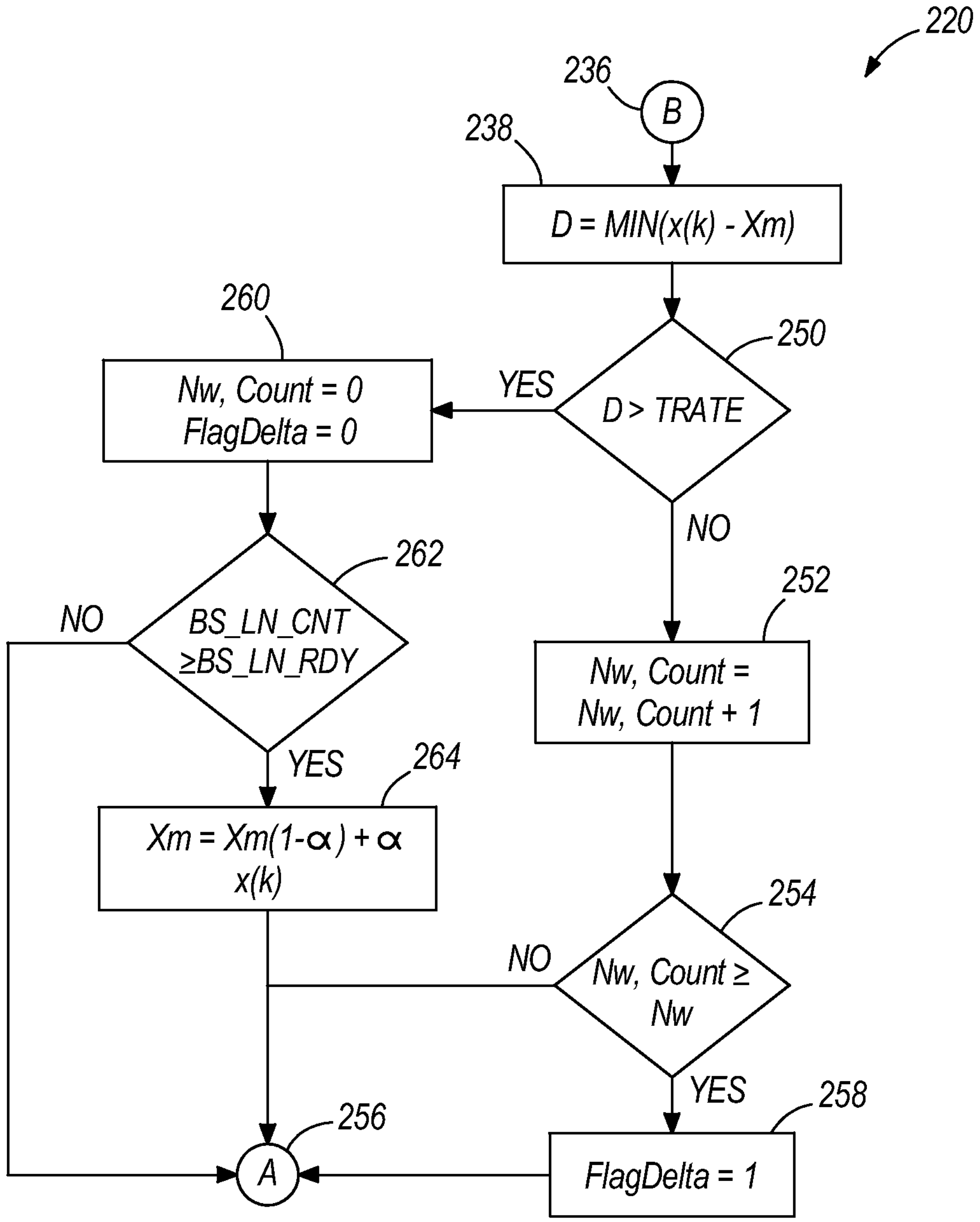
FIG. 16 illustrates a continuation of the flow chart of FIG. 15.

FIGS. 15 and 16 illustrate one embodiment of a method 220, comprising a continuous flow chart, under the disclosure for determining whether air is contained in a chamber of a pump. The method 220 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 220, and the alarm being turned on if the processor determines that air is contained in the chamber which may further shut down the pump. Moreover, the method 220 may utilize the clock of the drug delivery infusion system 100 of FIG. 1 to keep time of activities of the plunger or the sensor, and may use the positional sensor to determine a position of the plunger. In other embodiments, the method 220 may utilize varying components to implement the method.

In step 222, the method starts. After step 222, the method proceeds through location step 224 to step 226. In step 226, a force profile X(k) of the plunger is acquired for the first cycle of the plunger with k=1 representing the first cycle of the plunger. The force profile X(k) comprises a vector comprising the six forces on the plunger at each of the six positions/points of the plunger during the k cycle of the plunger. In other embodiments, the force profile may be acquired with a varying number of positions of the plunger. The method then proceeds to step 228 and increments the profile count PC using the equation PC=PC+1 with PC initially being O the first time through so that PC will be incremented to 1. The method then proceeds to step 230 and determines whether the profile count PC is less than or equal to the number of initial cycles of the plunger to ignore Ni which is set to Ni=2. In other embodiments, Ni may be set to other values.

If step 230 determines that the profile count PC is less than or equal to the number of initial cycles of the plunger to ignore Ni then the method proceeds back to and repeats steps 224, 226, 228, and 230 until the profile count PC is not less than or equal to the number of initial cycles of the plunger to ignore Ni at which point the method proceeds to step 232. In step 232 a determination is made as to whether the baseline count BS LN CNT is less than the baseline ready variable BS_LN_RDY. The baseline count BS_LN_CNT is initially set to BS_LN_CNT=0. The baseline ready variable BS_LN_RDY is set to BS_LN_RDY=5. In other embodiments, BS_LN_CNT and BS_LN_RDY may be set to other values. If step 232 determines that BS_LN_CNT is not less than BS_LN_RDY than the method proceeds through location step 234 of FIG. 15, through location step 236 of FIG. 16, to step 238 of FIG. 16 which is discussed later on.

If in step 232 a determination is made that the baseline count BS_LN_CNT is less than BS_LN_RDY than the method proceeds to step 240. In step 240 a determination is made as to whether the Analog-To-Digital-Count (ADC) at that instant is less than the primary threshold for fluid TPRI, and as to whether the profile count PC is greater than the number of initial cycles of the plunger to ignore plus 2 represented by PC being greater than Ni+2. The primary threshold for fluid TPRI is set to 3,000. In other embodiments, the primary threshold for fluid TPRI may be set to other values. If the determination in step 240 is made that either the Analog-To-Digital-Count (ADC) read by an air sensor downstream of the chamber is not less than the primary threshold for fluid TPRI (which means that air is in the chamber), or that the profile count PC is not greater than the number of initial cycles of the plunger to ignore plus 2 (there is a lag of 2 cycles due to the air sensor being located downstream of the chamber) represented by PC being greater than Ni+2, than the method proceeds to step 242, and determines whether the baseline count BS_LN_CNT is greater than 0. In other embodiments, the lag number of cycles used may vary. If step 242 determines that the baseline count BS_LN_CNT is not greater than 0 then the method proceeds back to location step 224 to step 226 and continues the loop. If step 242 determines that the baseline count BS_LN_CNT is greater than 0 then the method proceeds through location step 234 of FIG. 15, through location step 236 of FIG. 16, to step 238 of FIG. 16 which is discussed later on.

If in step 240 the determination is made that either the Analog-To-Digital-Count (ADC) read by an air sensor downstream of the chamber is less than the primary threshold for fluid TPRI (which means that liquid is in the chamber), and that the profile count PC is greater than the number of initial cycles of the plunger to ignore plus 2 (indicating that the lag of 2 cycles, due to the air sensor being located downstream of the chamber, has been completed) represented by PC being greater than Ni+2, then the method proceeds to step 244. In step 244, the accumulated baseline profile Xt is determined using the equation Xt=Xt+X(k−2) (wherein X(k−2) represents the force profile, expressed as a six point vector, for 2 cycles ago due to the air sensor being located downstream of the chamber) wherein Xt is initially set to O and k represents the number of the current cycle of the plunger. In other embodiments, the equation for Xt may be varied. After step 244, the method proceeds to step 246 and increments the baseline count BS_LN_CNT using the equation BS_LN_CNT=BS_LN_CNT+1. After step 246, the method proceeds to step 248 and determines the baseline force profile Xm, expressed as a 6 point vector, using the equation Xm=Xt I BS_LN_CNT which averages the force measurements on the plunger taken at times when liquid is in the chamber over the number of baseline count BS_LN_CNT cycles of the plunger. The baseline force profile Xm represents the baseline force vector for a situation in which liquid (fluid) is contained in the chamber 2 cycles prior to the current cycle due to the air sensor being located downstream of the chamber. In other embodiments, the baseline force profile Xm may be calculated using varying equations. After step 248, the method proceeds through location step 234 of FIG. 15, through location step 236 of FIG. 16, to step 238 of FIG. 16.

In step 238 of FIG. 16, the minimum distance D between the current vector force profile of the plunger and the baseline force vector is determined using the equation D=min(X(k)−Xm) where k represents the current cycle of the plunger and Xm represents the baseline force vector with D being the single minimum distance between the corresponding 6 points of the two vectors. After step 238, the method proceeds to step 250 and determines whether D is greater than a threshold for a given infusion rate Trate which is set to −0.3. In other embodiments, Trate may be set to a varying number depending on the infusion rate or other factors, such as the signal variance. Additionally, more than one value for Trate may be used to provide regions of high probability versus low probability. If a determination is made in step 250 that the minimum distance D between the current vector force profile of the plunger and the baseline force vector is not greater than the threshold for a given infusion rate Trate, which indicates that air is in the chamber, then the method proceeds to step 252.

In step 252, Nw count is incremented using the equation Nw count=Nw count+1 with Nw count initially set to 0. Nw count represents the current number of observed air cycles. After step 252, the method proceeds to step 254 and determines whether Nw count is greater than or equal to Nw with Nw representing the threshold number of consecutive observed air cycles of the plunger after which an air alarm will be turned on indicating that air is contained in the chamber. If a determination is made in step 254 that Nw count is not greater than or equal to Nw than the method proceeds through location step 256 back to location step 224 of FIG. 15 to step 226 of FIG. 15 and repeats the loop. If a determination is made in step 254 that Nw count is greater than or equal to Nw than the method proceeds to step 258, sets Flag Delta to 1 indicating that air is present in the chamber, turns on an alarm to indicate that air is present in the chamber, and proceeds through location step 256 back to location step 224 of FIG. 15 to step 226 of FIG. 15 and repeats the loop. Step 258 may further comprise shutting down the pump.

If a determination is made in step 250 that the minimum distance D between the current vector force profile of the plunger and the baseline force vector is greater than the threshold for a given infusion rate Trate, indicating that liquid is contained in the chamber, then the method proceeds to step 260. In step 260, Nw count is reset to O with Nw count representing the current number of observed air cycles, and Flag Delta is also reset to O with Flag Delta representing that air is present in the chamber. After step 260, the method proceeds to step 262 and determines whether the baseline count BS_LN_CNT is greater than or equal to the baseline ready variable BS_LN_RDY which is set to BS LN ROY=5. In other embodiments, the baseline ready variable BS_LN_RDY may be set to other values.

If a determination is made in step 262 that the baseline count BS_LN_CNT is not greater than or equal to the baseline ready variable BS_LN_RDY then the method proceeds through location step 256 back to location step 224 of FIG. 15 to step 226 of FIG. 15 and repeats the loop. If a determination is made in step 262 that the baseline count BS_LN_CNT is greater than or equal to the baseline ready variable BS_LN_RDY then the method proceeds to step 264. In step 264 the baseline force profile Xm, expressed as a 6 point vector, is calculated using an adaptive baseline force profile equation Xm=Xm*(1−a)+a*X(k) wherein a comprises a forgetting rate which determines what percentage of the calculated baseline force profile Xm comprises the preceding calculated baseline force profile Xm and what percentage of the baseline force profile Xm comprises the current force profile X(k) where X(k) is the current force profile of the plunger for the k cycle of the plunger. In one embodiment the forgetting rate a may be set to 0.1. In other embodiments, the forgetting rate a may be set to varying values. The adaptive baseline may be determined in alternate manners such as a moving average or Kalman filter.

Step 264 comprises an adaptive baseline step which allows the user to assert control over the baseline force profile Xm by controlling the forgetting rate a. In other embodiments, the forgetting rate a may be pre-programmed. In still other embodiments, varying ways may be used to calculate the baseline force profile Xm. After step 264 the method proceeds through location step 256 back to location step 224 of FIG. 15 to step 226 of FIG. 15 and repeats the loop. In other embodiments, one or more steps of the method 220 may be modified, not followed, or one or more additional steps may be added. Moreover, any of the variables of the method 220 may be either user set, using an input device, or pre-set into the processor.

Figure 17:
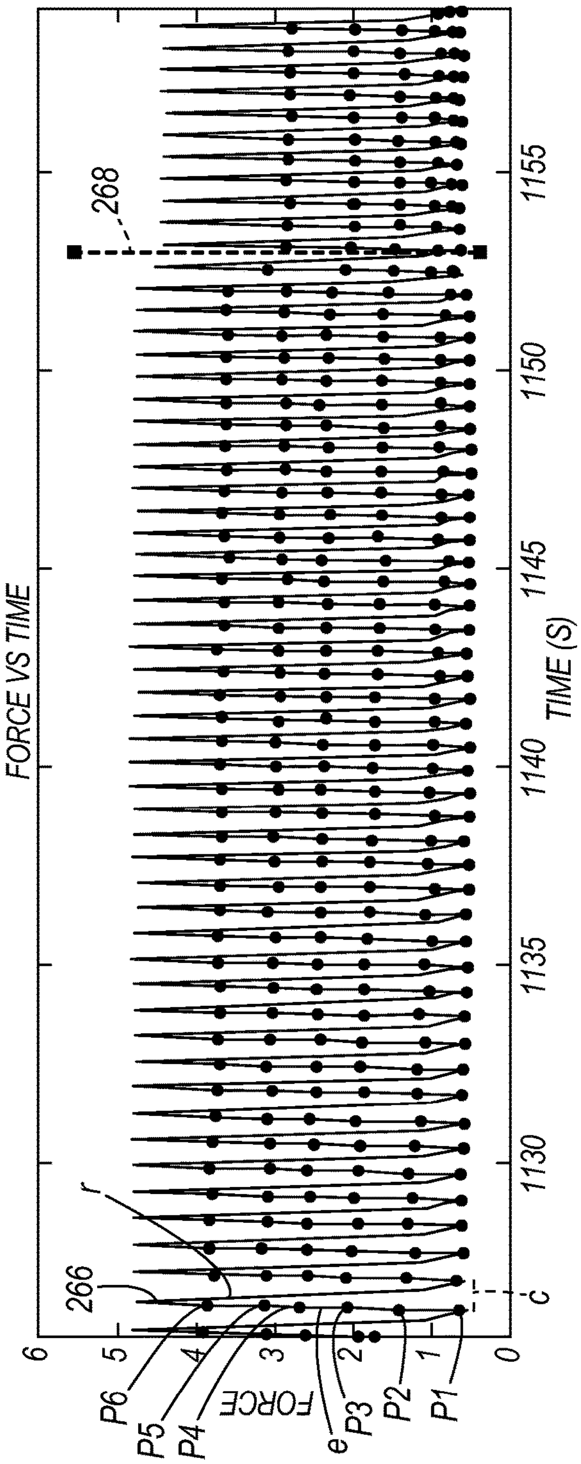
FIG. 17 illustrates a representative graph for one embodiment plotting a force sensor profile.

FIG. 17 illustrates a representative graph for one embodiment plotting a force sensor profile 266. The Y-axis represents pounds of force on the plunger detected by a plunger force sensor and the X-axis represents time in seconds. Six points p1-p6 are calculated during the expansion portion e of each cycle c of the plunger. No points are sampled during the retraction portion r of each cycle c of the plunger. Line 268 represents the point, during the fortyfifth cycle of the plunger, at which an air alarm is turned on due to air being in the chamber when the method 220 of FIGS. 15 and 16 is applied which is discussed more thoroughly below.

Figure 18:
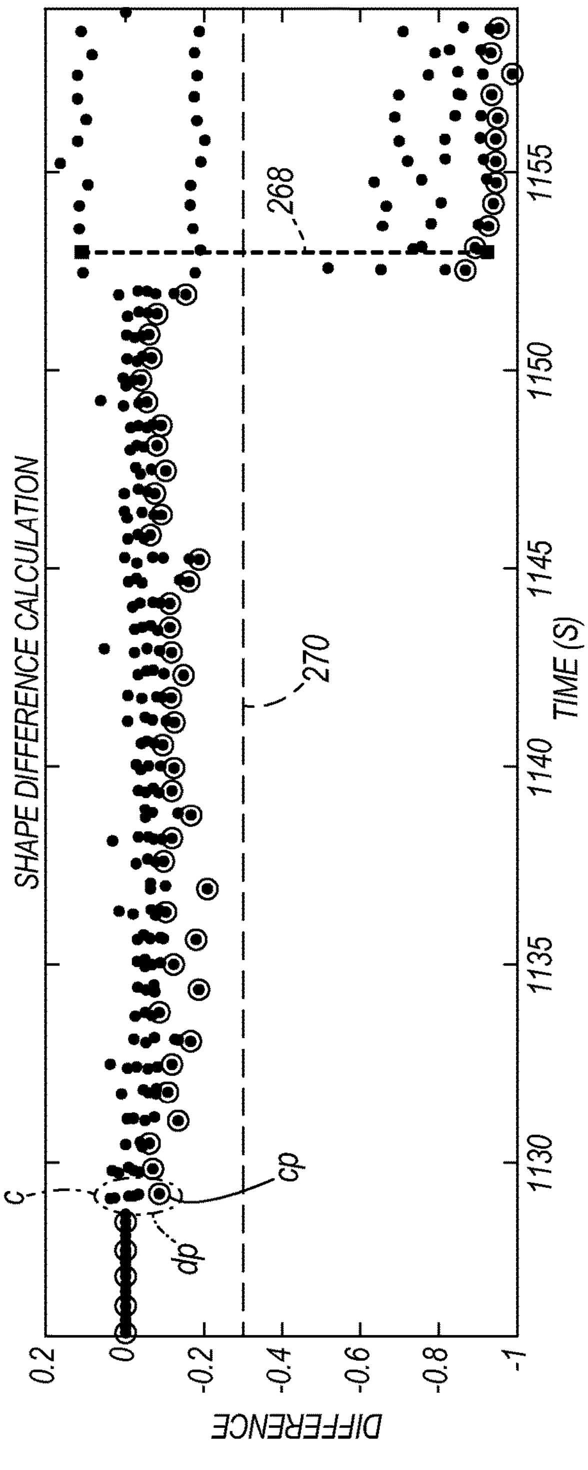
FIG. 18 illustrates a graph plotting for each cycle of the plunger of FIG. 17 six respective difference points representing the measured differences between a baseline, comprising liquid being in the chamber, and the corresponding points of each respective cycle of the plunger.

FIG. 18 illustrates a graph plotting for each cycle c of the plunger of FIG. 17 six respective difference points dp representing the measured differences between a baseline, comprising liquid being in the chamber, and the corresponding points of each respective cycle of the plunger. The Y-axis represents the differences and the X-axis represents time. The circled points cp represent the minimum difference for each cycle of the plunger between the six respective difference points dp of each cycle of the plunger and the baseline. Line 270 represents the threshold for a given infusion rate Trate which is set to −0.3. As discussed more thoroughly below, when the method 220 of FIGS. 15 and 16 is applied, the method determines that liquid is contained in the chamber during the first forty-three cycles of the plunger, determines that air is in the chamber during the forty-fourth cycle of the plunger, and after line 268, as it does in FIG. 17, turns on an air alarm during the forty-fifth cycle of the plunger representing that air is in the chamber.

Figure 19:
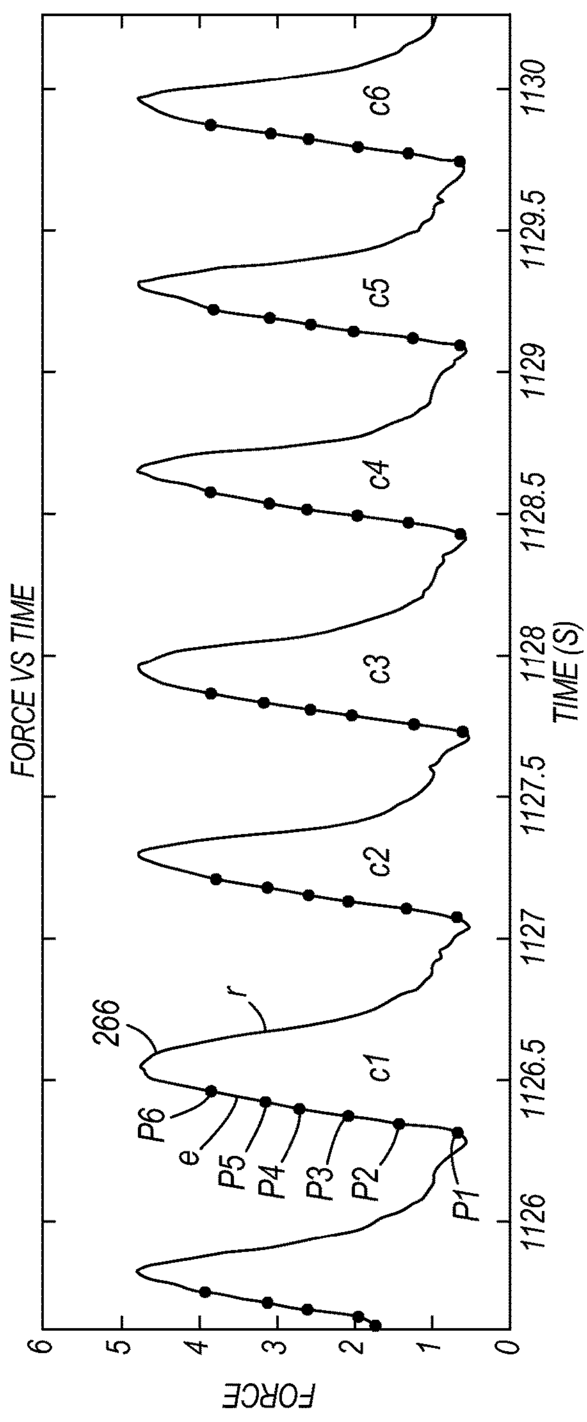
FIG. 19 illustrates a graph plotting the first six full cycles of the force sensor profile of FIG. 17.

FIG. 19 illustrates a graph plotting the first six full cycles C1-C6 of the force sensor profile 266 of FIG. 17. The Y-axis represents pounds of force on the plunger detected by a plunger force sensor and the X-axis represents time in seconds. Six points p1-p6 are calculated during the expansion portion e of each cycle c of the plunger. No points are sampled during the retraction portion r of each cycle c of the plunger.

Figure 20:
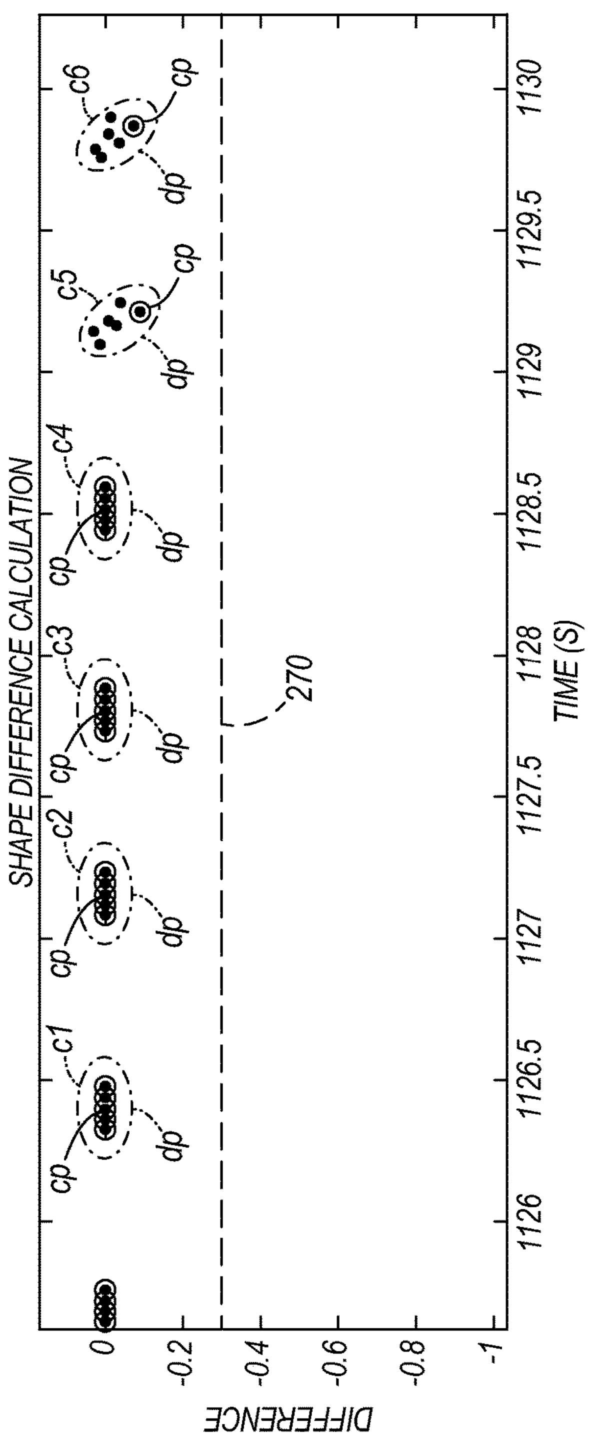
FIG. 20 illustrates a graph plotting for each of the first six full cycles of the plunger of FIG. 18 six respective difference points representing the measured differences between a baseline, comprising liquid being in the chamber, and the corresponding points of each respective cycle of the plunger.

FIG. 20 illustrates a graph plotting for each of the first six full cycles C1-C6 of the plunger of FIG. 18 six respective difference points dp representing the measured differences between a baseline, comprising liquid being in the chamber, and the corresponding points of each respective cycle of the plunger. The Y-axis represents the differences and the X-axis represents time. The circled points cp represent the minimum difference for each cycle of the plunger between the six respective difference points dp of each cycle of the plunger and the baseline. Line 270, as it does in FIG. 18, represents the threshold for a given infusion rate Trate which is set to −0.3. As discussed more thoroughly below, when the method of FIGS. 15 and 16 is applied the method determines that liquid is contained in the chamber during each of the first six full cycles C1-C6 of the plunger.

Figure 21:
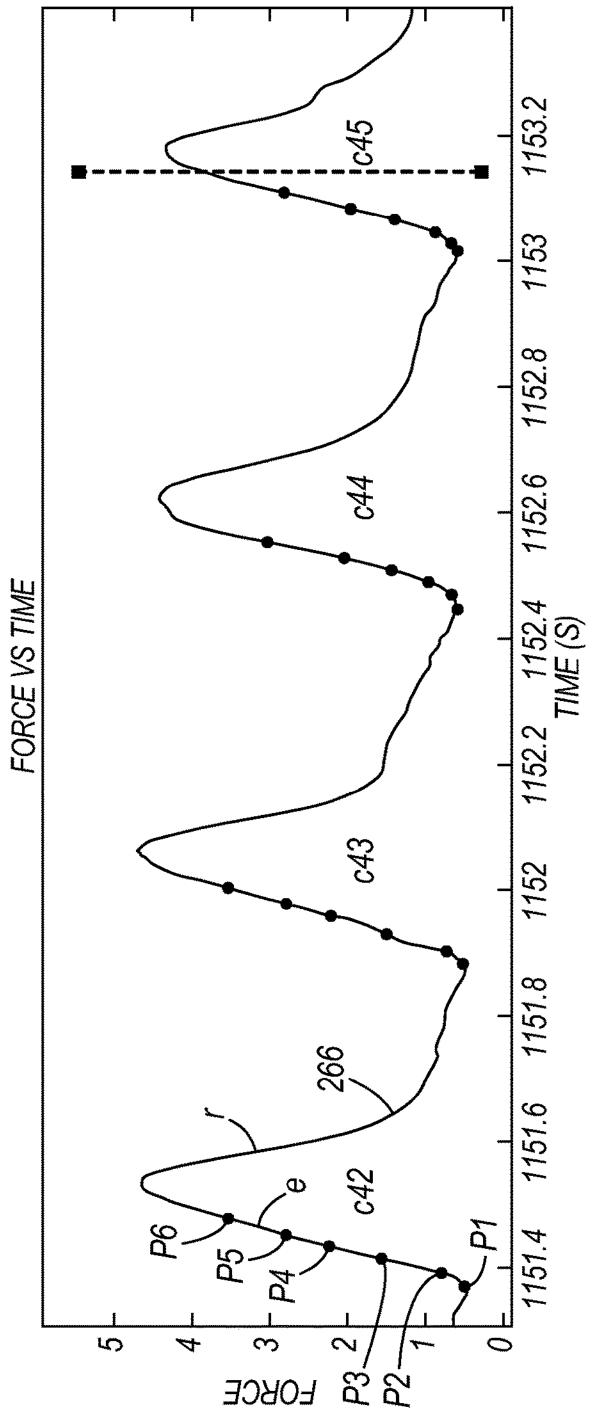
FIG. 21 illustrates a graph plotting the forty-second through forty-fifth cycles of the force sensor profile of FIG. 17.

FIG. 21 illustrates a graph plotting the forty-second through forty-fifth cycles C42-C45 of the force sensor profile 266 of FIG. 17. The Y-axis represents pounds of force on the plunger detected by a plunger force sensor and the X-axis represents time in seconds. Six points p1-p6 are calculated during the expansion portion e of each cycle c of the plunger. No points are sampled during the retraction portion r of each cycle c of the plunger.

Figure 22:
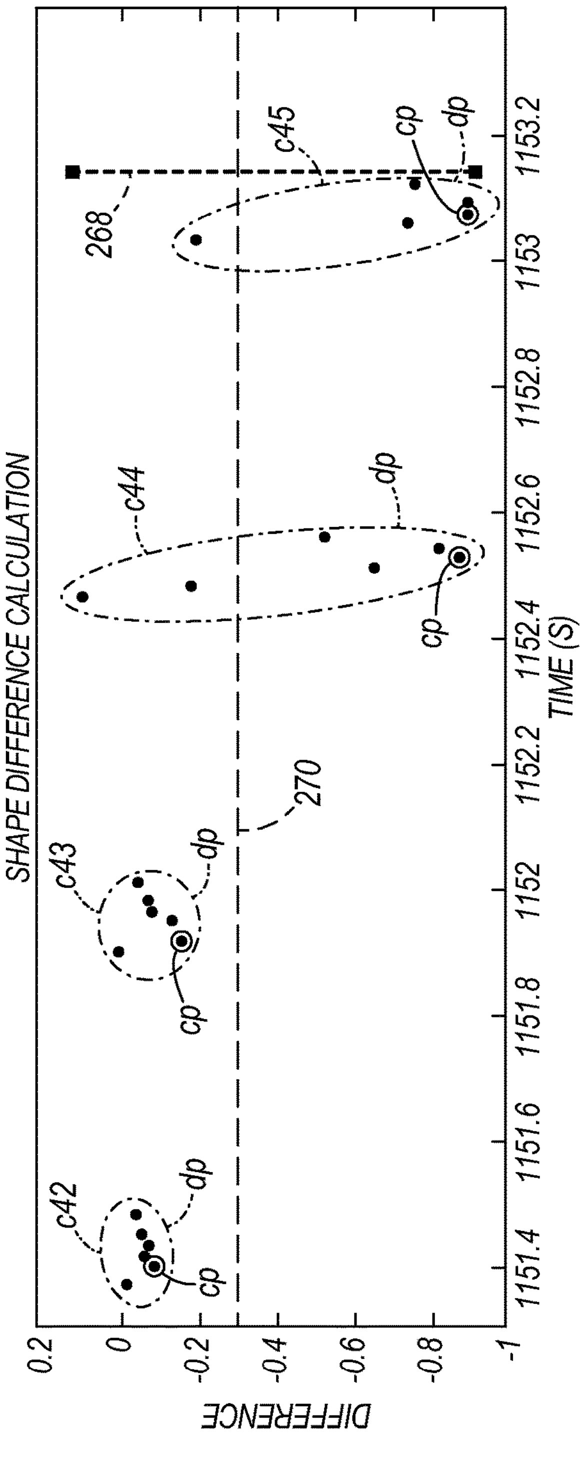
FIG. 22 illustrates a graph plotting for the forty-second through forty-fifth cycles of the plunger of FIG. 18 six respective difference points representing the measured differences between a baseline, comprising liquid being in the chamber, and the corresponding points of each respective cycle of the plunger.

FIG. 22 illustrates a graph plotting for the forty-second through forty-fifth cycles C42-C45 of the plunger of FIG. 18 six respective difference points dp representing the measured differences between a baseline, comprising liquid being in the chamber, and the corresponding points of each respective cycle of the plunger. The Y-axis represents the differences and the X-axis represents time. The circled points cp represent the minimum difference for each cycle of the plunger between the six respective difference points dp of each cycle of the plunger and the baseline. Line 270, as it does in FIGS. 18 and 20, represents the threshold for a given infusion rate Trate which is set to −0.3. As discussed more thoroughly below, when the method 220 of FIGS. 15 and 16 is applied, the method determines that liquid is contained in the chamber during the first forty-three cycles of the plunger, determines that air is in the chamber during the forty-fourth cycle of the plunger, and after line 268, as it does in FIG. 17, turns on an air alarm during the forty-fifth cycle of the plunger representing that air is in the chamber.

The method 220 of FIGS. 15 and 16 will now be applied to the example of FIGS. 17-22 to demonstrate how the method works. In the interest of efficiency, only some of the steps of the method 220 are described below. When the method 220 of FIGS. 15 and 16 is applied to the example of FIGS. 17-22, the first two cycles C1 and C2 are skipped because the profile count PC of 1 and 2 respectively is less than or equal to Ni=2. The force profiles X(k) for the third and fourth cycles C3 and C4 are acquired but not used because the profile count PC of 3 and 4 respectively is not greater than the number of initial cycles of the plunger to ignore (Ni=2) plus 2 represented by PC being greater than 4 (Ni+2=2+2=4). When the profile count PC reaches 5 at the fifth cycle C5, the accumulated baseline profile Xt is determined because the measured ADC of 1,673 is less than the primary threshold for fluid TPRI of 3,000, and the profile count PC=5 is greater than 4 (Ni+2=2+2=4). At this point in time, the baseline force profile Xm, expressed as a six point vector, is calculated using the equation Xm=Xt/BS_LN_CNT wherein Xt=Xt [which is initially set to 0]+X (k−2) =0+X (5-2)=0+X(3)=X(3) [representing the force profile for the third cycle] and BS_LN_CNT=BS_LN_CNT [which is initially set to 0]+1=0+1=1. Applying this equation results in the baseline force profile, expressed as a six point force vector, being Xm=(0.574252, 1.192627, 1.990768, 2.551261, 3.144921, 3.823651). The method 220 then determines the minimum distance D between the current vector force profile X(k), where k=5, of the plunger and the baseline force vector using the equation D=min(X(k)−Xm) =min(X(5)−Xm)=min ((0.574252, 1.192627, 1.990768, 2.551261, 3.144921, 3.823651)−(0.601876, 1.226866, 1.968040, 2.542253, 3.058266, 3.787412)) =min ((0.574252−0.601876), (1.192627−1.226866), (1.990768−1.968040), (2.551261−2.542253), (3.144921−3.058266), (3.823651−3.787412))=min (0.027624, 0.034239, −0.022727, −0.009008, −0.086655, −0.036239)=−0.086655. Because D=−0.086655 is greater than Trate=−0.3, the method determines that the current cycle/profile is for liquid being in the chamber, and the adaptive baseline, using the forgetting rate a, is not applied because the baseline count BS_LN_CNT=1 is not greater than or equal to the baseline ready variable BS LN ROY=5.

For the sixth cycle C6 the profile count PC increases to 6 and the accumulated baseline profile Xt is determined because the measured ADC of 1,740 is less than the primary threshold for fluid TPRI of 3,000, and the profile count PC=6 is greater than 4 (Ni+2=2+2=4). At this point in time, the baseline force profile Xm, expressed as a six point vector, is calculated using the equation Xm=Xt I BS_LN_CNT wherein Xt=Xt+X(k−2) and BS_LN_CNT=2. Applying this equation results in the baseline force profile, expressed as a six point force vector, being Xm=(0.584984, 1.234167, 1.947920, 2.556566, 3.103720, 3.818871). The method 220 then determines the minimum distance D between the current vector force profile X(k), where k=6, of the plunger and the baseline force vector using the equation D=min(X(k)−Xm)=min(X(6)−Xm)=min ((0.600387, 1.266444, 1.916179, 2.547273, 3.031686, 3.805076)−(0.584984, 1.234167, 1.947920, 2.556566, 3.103720, 3.818871))=min ((0.600387−0.584984), (1.266444−1.234167), (1.916179−1.947920), (2.547273−2.556566), (3.031686−3.103720), (3.805076−3.818871))=min (0.015402, 0.032277, −0.031741, −0.009293, −0.072035, −0.013795)=−0.072035. Because D=−0.072035 is greater than Trate=−0.3, the method determines that the current cycle/profile is for liquid being in the chamber, and the adaptive baseline, using the forgetting rate a, is not applied because the baseline count BS_LN_CNT=2 is not greater than or equal to the baseline ready variable BS_LN_RDY=5.

When the method reaches the forty-third cycle C43 (the intermediate cycle calculations are not described here in the interest of efficiency) the profile count PC increases to 43 and the accumulated baseline profile Xt is determined because the measured ADC is less than the primary threshold for fluid TPRI of 3,000, and the profile count PC=43 is greater than 4 (Ni+2=2+2=4). At this point in time, the baseline force profile Xm, expressed as a six point vector, is calculated using the equation Xm=Xt I BS_LN_CNT wherein Xt=Xt+X(k−2) and BS_LN_CNT=39. Applying this equation results in the baseline force profile, expressed as a six point force vector, being Xm=(0.507904, 0.882215, 1.642329, 2.326609, 2.893227, 3.623199). The method 220 then determines the minimum distance D between the current vector force profile X(k), where k=43, of the plunger and the baseline force vector using the equation D=min(X (k)−Xm)=min(X(43)−Xm)=min ((0.521021, 0.729376, 1.515777, 2.249448, 2.828867, 3.582641)−(0.507904, 0.882215, 1.642329, 2.326609, 2.893227, 3.623199))=min ((0.521021−0.507904), (0.729376−0.882215), (1.515777−1.642329), (2.249448−2.326609), (2.828867−2.893227), (3.582641−3.623199))=min (0.013117, −0.152839, −0.126552, −0.077161, −0.064360, −0.040558)=−0.152839. Because D=−0.152839 is greater than Trate=−0.3, the method determines that the current cycle/profile is for liquid being in the chamber, and the adaptive baseline, using the forgetting rate a, is determined because the baseline count BS_LN_CNT=39 is greater than or equal to the baseline ready variable BS_LN_RDY=5. Applying the forgetting rate a=0.100000 to calculate the adaptive baseline results in the adaptive baseline Xm=Xm*(1−a)+a*X(k)=(0.509216, 0.866931, 1.629673, 2.318893, 2.886791, 3.619144).

When the method reaches the forty-fourth cycle C44 the profile count PC increases to 44 and the accumulated baseline profile Xt is determined because the measured ADC is less than the primary threshold for fluid TPRI of 3,000, and the profile count PC=44 is greater than 4 (Ni+2=2+2=4). At this point in time, the baseline force profile Xm, expressed as a six point vector, is calculated using the equation Xm=Xt I BS_LN_CNT wherein Xt=Xt+X(k−2) and BS_LN_CNT=40. Applying this equation results in the baseline force profile, expressed as a six point force vector, being Xm=(0.509216, 0.866931, 1.629673, 2.318893, 2.886791, 3.619144). The method 220 then determines the minimum distance D between the current vector force profile X(k), where k=44, of the plunger and the baseline force vector using the equation D=min(X(k)−Xm)=min(X(44)−Xm)=min ((0.616675, 0.690732, 0.974907, 1.446447, 2.064309, 3.097704)−(0.509216, 0.866931, 1.629673, 2.318893, 2.886791, 3.619144))=min ((0.616675−0.509216), (0.690732−0.866931), (0.974907−1.629673), (1.446447−2.318893), (2.064309−2.886791), (3.097704−3.619144))=min (0.107459, −0.176199, −0.654767, −0.872446, −0.822482, −0.521439)=−0.872446. Because D=−0.872446 is not greater than Trate=−0.3, the method determines that the current cycle/profile is for air being in the chamber and increments Nw count to Nw count+1=O+1=1.

When the method reaches the forty-fifth cycle C45 the profile count PC increases to 45 and the accumulated baseline profile Xt is determined because the measured ADC is less than the primary threshold for fluid TPRI of 3,000, and the profile count PC=45 is greater than 4 (Ni+2=2+2=4). At this point in time, the baseline force profile Xm, expressed as a six point vector, is calculated using the equation Xm=Xt I BS_LN_CNT wherein Xt=Xt+X(k−2) and BS_LN_CNT=41. Applying this equation results in the baseline force profile, expressed as a six point force vector, being Xm=(0.509216, 0.866931, 1.629673, 2.318893, 2.886791, 3.619144). The method 220 then determines the minimum distance D between the current vector force profile X(k), where k=45, of the plunger and the baseline force vector using the equation D=min(X(k)−Xm)=min(X(44)−Xm)=min ((0.613084, 0.674059, 0.891756, 1.421075, 1.990083, 2.859728)−(0.509216, 0.866931, 1.629673, 2.318893, 2.886791, 3.619144))=min ((0.613084−0.509216), (0.674059−0.866931), (0.891756−1.629673), (1.421075−2.318893), (1.990083−2.886791), (2.859728−3.619144))=min (0.103868, −0.192872, −0.737917, −0.897818, −0.896708, −0.759415)=−0.897818. Because D=−0.897818 is not greater than Trate=−0.3, the method determines that the current cycle/profile is for air being in the chamber, increments Nw count to Nw count+1=1+1=2, sets FlagDelta=1, and signals an air alarm indicating that air is in the chamber.

The method of FIGS. 15 and 16 was implemented to analyze a large number of data sets for a variety of flow rates. The testing resulted in no false negative occurrences.

Figure 23:
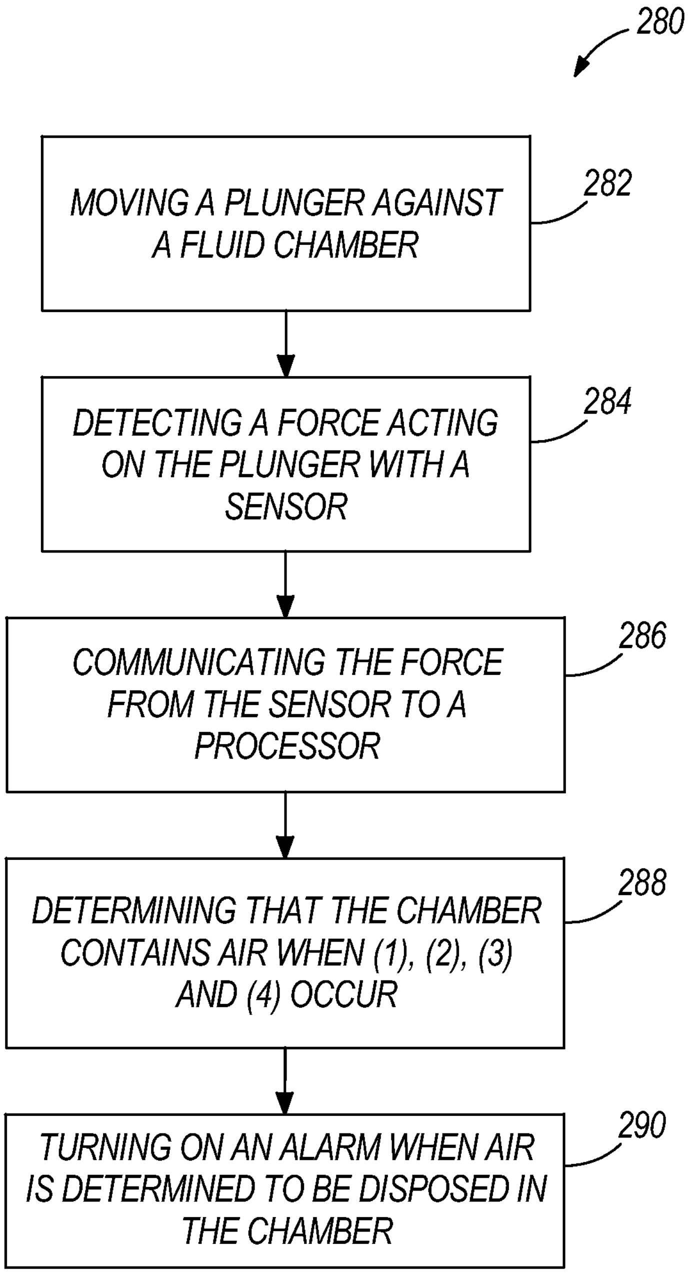
FIG. 23 illustrates a flowchart for one embodiment of a method for detecting air in a chamber of an infusion system.

FIG. 23 illustrates a flowchart for one embodiment of a method 280 for detecting air in a chamber of an infusion system. The method 280 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 280, and the alarm being turned on if the processor determines that air is contained in the chamber which may trigger the pump being shut down. Moreover, the method 280 may utilize the clock of the drug delivery infusion system 100 of FIG. 1 to keep time of activities of the plunger or the sensor, and may use the positional sensor to determine a position of the plunger, with each being in electronic communication with the processor. In other embodiments, the method 280 may utilize varying components to implement the method.

In step 282 a plunger is moved, with an actuator device, acting against a chamber containing fluid. In step 284, a sensor is used to detect a force acting on the plunger as it moves against the chamber. In step 286 a measurement of the force is electronically communicated from the sensor to a processor. In step 288 the processor determines: (1) a baseline force profile; (2) a current force profile representing the current force acting on the plunger against the chamber; (3) a difference between the current force profile and the baseline force profile; and (4) that the chamber contains air when the calculated difference crosses a threshold. In step 290 the processor turns on an alarm when the processor determines that the chamber contains the air. Step 290 may further comprise shutting down the pump when the alarm is turned on.

In one embodiment, the baseline force profile represents the chamber being filled with the fluid. In another embodiment, the processor determines the baseline force profile by taking force measurements at a plurality of plunger positions over a cycle of the plunger against the chamber. In an additional embodiment, the processor determines the baseline force profile by averaging force measurements taken over a plurality of cycles of the plunger against the chamber. In yet another embodiment, the processor determines the baseline force by additionally taking into account the current force profile acting on the plunger during a current cycle of the plunger against the chamber.

In still another embodiment, the processor further applies a forgetting rate, moving average or Kalman filter which controls what portion of the updated baseline force profile is made up of the average or estimated baseline force measurements and what portion of the updated baseline force profile is made up of the current force profile. In an additional embodiment, the processor determines the current force profile by taking force measurements at a plurality of plunger positions over a current cycle of the plunger against the chamber. In another embodiment, the processor calculates the difference between the current force profile and the baseline force profile by calculating respective differences between a plurality of points of the current force profile relative to a respective plurality of points of the baseline force profile, and determining a minimum difference of the respective differences or an absolute maximum difference of the respective differences. In an additional embodiment, the processor determines that the chamber contains the air when the minimum difference is less than the threshold. In still another embodiment, the processor determines that the chamber contains the air when the calculated difference is below the threshold. In other embodiments, any of the steps of the method 280 may be altered, not followed, or additional steps may be added.

Figure 24:
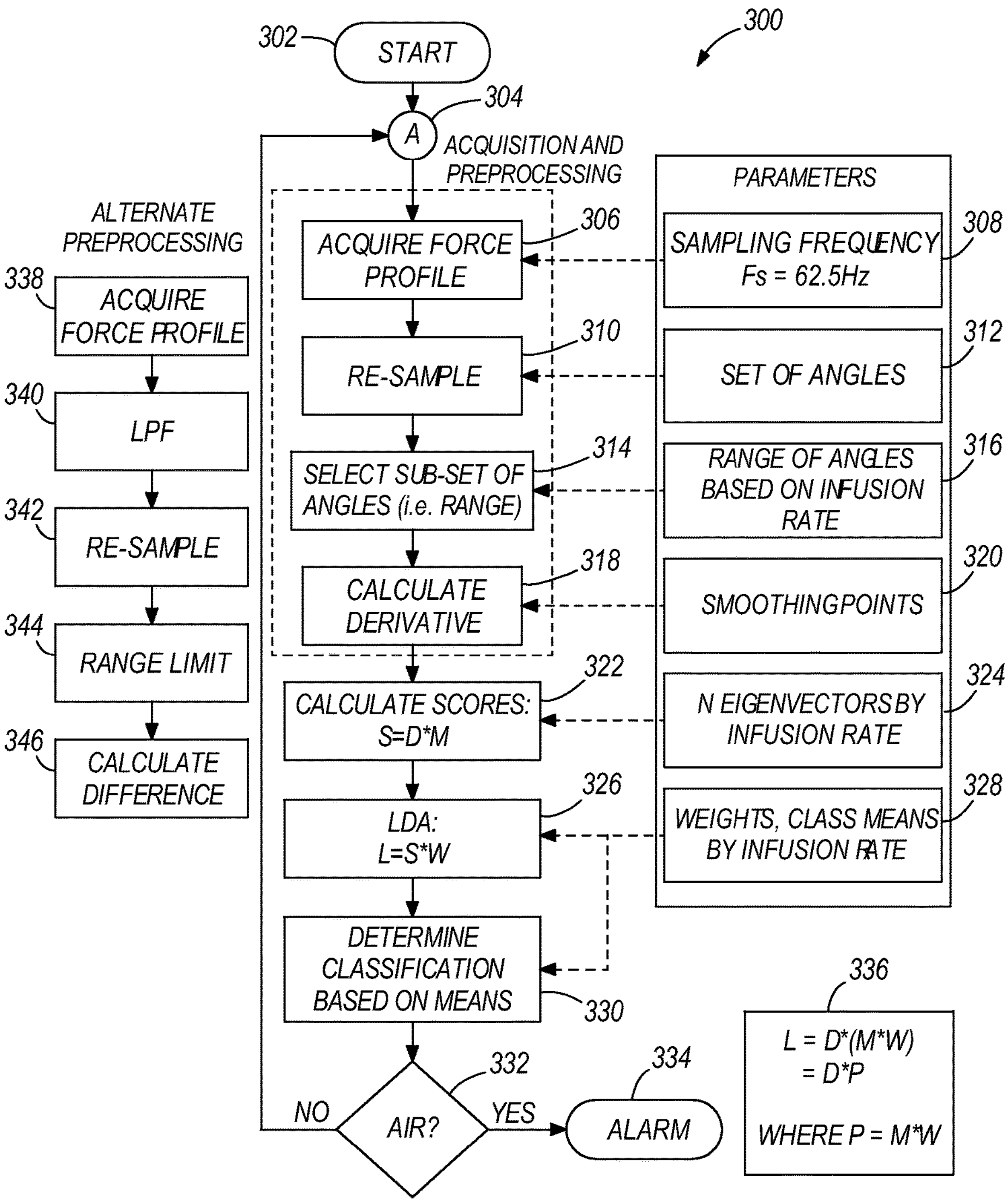
FIG. 24 illustrates one embodiment of a method, comprising a continuous flow chart, for determining whether air is contained in a chamber of a pump based upon a shape of the plunger force profile.

FIG. 24 illustrates one embodiment of a method 300, comprising a continuous flow chart, under the disclosure for determining whether air is contained in a chamber of a pump based upon a shape of the plunger force profile. The method 300 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 300, and the alarm being turned on if the processor determines that air is contained in the chamber which may trigger the pump being shut down. Moreover, the method 300 may utilize the clock of the drug delivery infusion system 100 of FIG. 1 to keep time of activities of the plunger or the sensor, and may use the positional sensor to determine a position of the plunger. In other embodiments, the method 300 may utilize varying components to implement the method.

In step 302, the method 300 starts. After step 302, the method proceeds through location step 304 to step 306. In step 306 a force profile over one cycle of a plunger of the chamber is acquired using the sensor. In one embodiment, as shown in box 308, the sampling frequency may be 62.5 Hz. In other embodiments, varying parameters may be used. After step 306, the method proceeds to step 310 and re-samples the force profile for the cycle of the plunger at uniform increments with respect to position or at specific positions. In one embodiment, as shown in box 312, the re-sampling may take place over a set of angles and may be performed using linear, quadratic or cubic interpolation. In other embodiments, varying parameters may be used. After step 310, the method proceeds to step 314 and selects a sub-set of angles (i.e. one or more ranges). In one embodiment, as shown in box 316, the sub-set of angles may comprise a range of angles based on the infusion rate. In other embodiments, varying parameters may be used. After step 314, the method proceeds to step 318 and calculates a derivative. In one embodiment, as shown in box 320, this step may comprise simultaneously applying a smoothing operation. In other embodiments, this step may comprise applying varying parameters. Steps 306 through 318 comprise acquisition and preprocessing steps.

After step 318, the method proceeds to step 322 and calculates scores using the equation S=D*M where D comprises the derivative and M comprises a set of N eigenvectors by infusion rate, as shown in box 324, calculated using principal component analysis. In one embodiment, N=8. In other embodiments, the scores may be calculated using varying parameters. After step 322, the method proceeds to step 326 and applies a linear determinate analysis to calculate L=S*W where L represents the linear determinate result, S represents the scores, and W, as shown in box 328, represents weights of the linear discriminate analysis. In one embodiment, as shown in box 328, this step may also consider class means by infusion rate. In other embodiments, varying parameters may be used. After step 326, the method proceeds to step 330 and determines a classification based on the result of the linear discriminate analysis. This step may also consider class means by infusion rate as shown in box 328. After step 330, the method proceeds to step 332 and determines whether air is in the chamber based on the classification. If step 332 determines that air is contained in the chamber then the method proceeds to step 334 and sounds an air alarm during which the pump may be shut down. If step 332 determines that air is not in the chamber based on the classification then the method proceeds back to location step 304.

In an alternative embodiment, instead of steps 322 and steps 326 a linear determinate analysis may be conducted, as shown in box 336, using the equation L=D*(M*W)−D*P wherein P=M*W and the variables are identical to those described above. In another alternative embodiment, instead of steps 306 through steps 318, preprocessing steps 338, 340, 342, 344, and 346 may be followed. In step 338, a force profile of the plunger over one cycle of a plunger of the chamber is acquired using the sensor. In one embodiment, as shown in box 308, the sampling frequency may be 62.5 Hz. In other embodiments, varying parameters may be used. In step 340, a low pass filter is applied. In step 342, a re-sampling is done. In one embodiment, as shown in box 312, the re-sampling may take place over a set of angles. In other embodiments, varying parameters may be used. In step 344, a range limit is applied. In one embodiment, as shown in box 316, a sub-set of angles comprising a range of angles based on the infusion rate. In other embodiments, varying parameters may be used. In step 346, a difference is calculated. In one embodiment, this difference may comprise determining differences in points of the force profile. In other embodiments, this difference may use varying parameters.

Figure 25:
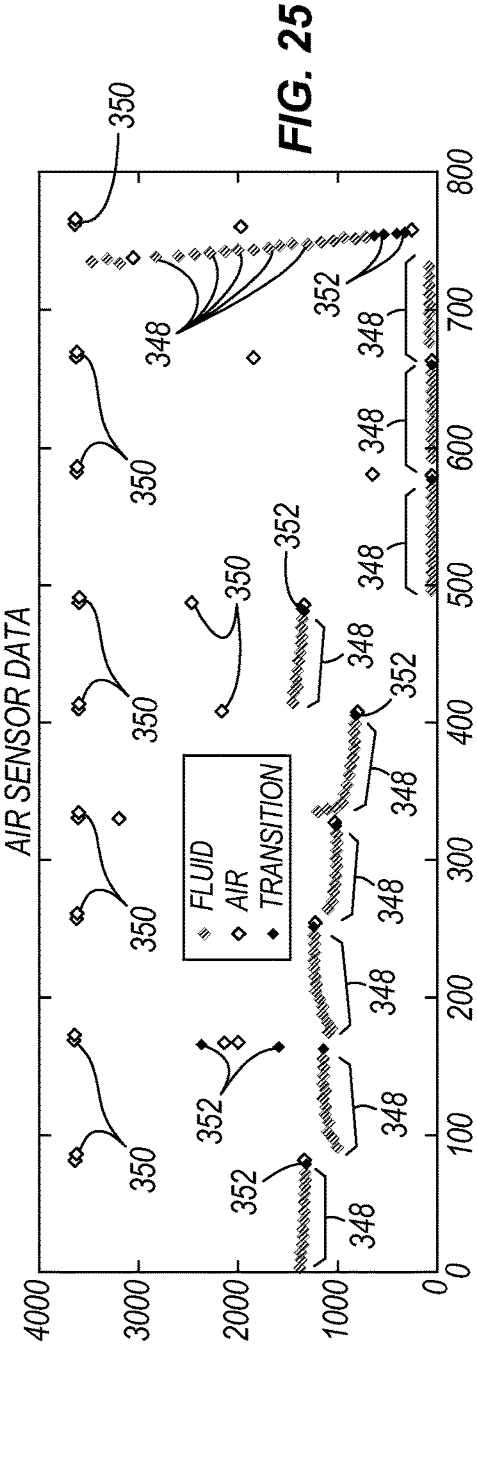
FIG. 25 illustrates a graph plotting air sensor data comprising representative points for each of fluid, air, and a transition.

FIG. 25 illustrates a graph plotting air sensor data comprising representative points for each of fluid 348, air 350, and transition 352. The Y axis represents an ADC count of the fluid of the chamber measured by a sensor and the X-axis represents sample number. The graph provides the observed air sensor ADC readings versus sample number over 1 O aggregated runs. Each run ends with a transition from fluid to air. The fluid readings (hashed symbols) 348, are clearly differentiated from those associated with air (open symbols) 350. Points that are close to or on a transition region from air to fluid are marked by solid symbols 352.

Figure 26:
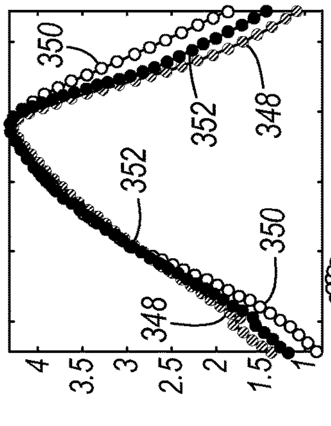
FIG. 26 illustrates a graph plotting average force profiles on the plunger corresponding to the embodiment of FIG. 28 for each of fluid, air, and a transition.

FIG. 26 illustrates a graph plotting force average profiles on the plunger corresponding to the embodiment of FIG. 25 for each of fluid 348, air 350, and transition 352. The graph demonstrates systematic differences in the average force associated with the three states (fluid 348, air 350, and transition 352) of FIG. 25. The Y-axis represents force and the X-axis represents an angular position of the motor powering the plunger.

Figure 27:
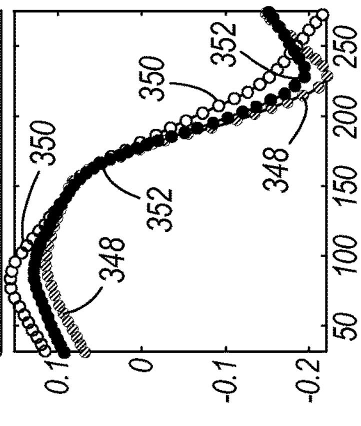
FIG. 27 illustrates a graph plotting derivatives of the force profiles on the plunger corresponding to the embodiment of FIGS. 26 and 28 for each of fluid, air, and a transition.
Figure 28:
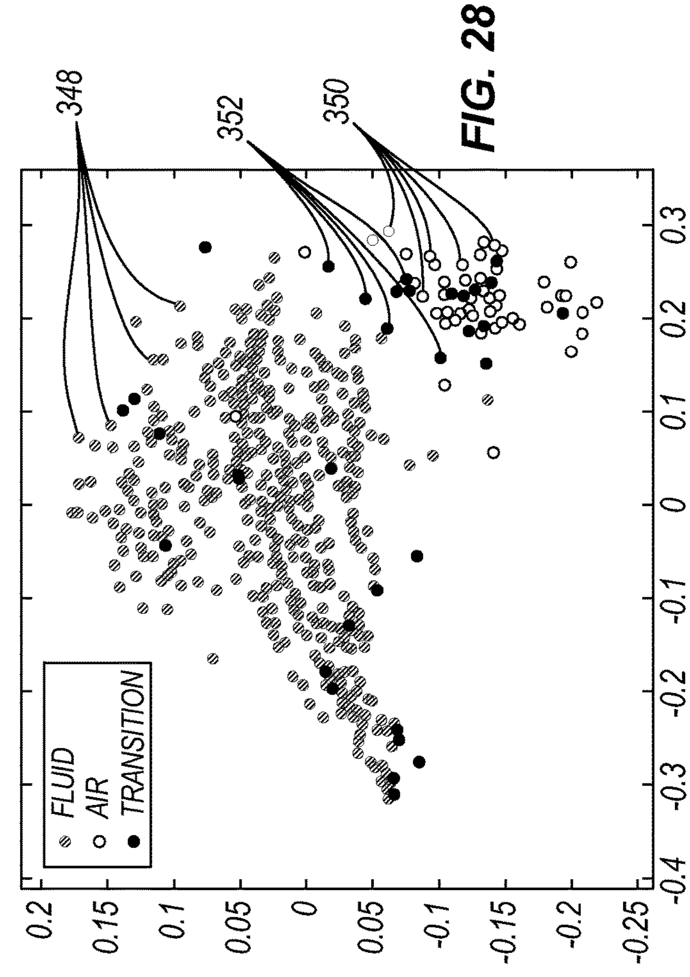
FIG. 28 illustrates a graph applying a principal component analysis plotting representative points at an infusion rate of 2 milliliters per hour.

FIG. 27 illustrates a graph plotting derivatives of the force profiles on the plunger corresponding to the embodiment of FIGS. 26 and 28 for each of fluid 348, air 350, and transition 352. The Y-axis represents a derivative of the force and the X-axis represents an angular position of the motor powering the plunger. The graph demonstrates that the systematic differences between the three states of FIG. 28 can be enhanced and differentiated from mechanism specific variation through the application of the first derivative.

FIG. 28 illustrates a graph applying a principal component analysis to plot representative points at an infusion rate of 2 milliliters per hour, with hashed symbols representing fluid points 348, open symbols representing points associated with air 350, and solid points representing transitional (indeterminant) points 352. The Y-axis represents score 4 and the X-axis represents score 2. The two dimensional view provided in the plot demonstrates a good separation across multiple actuators, fluids, and sets.

Figure 29:
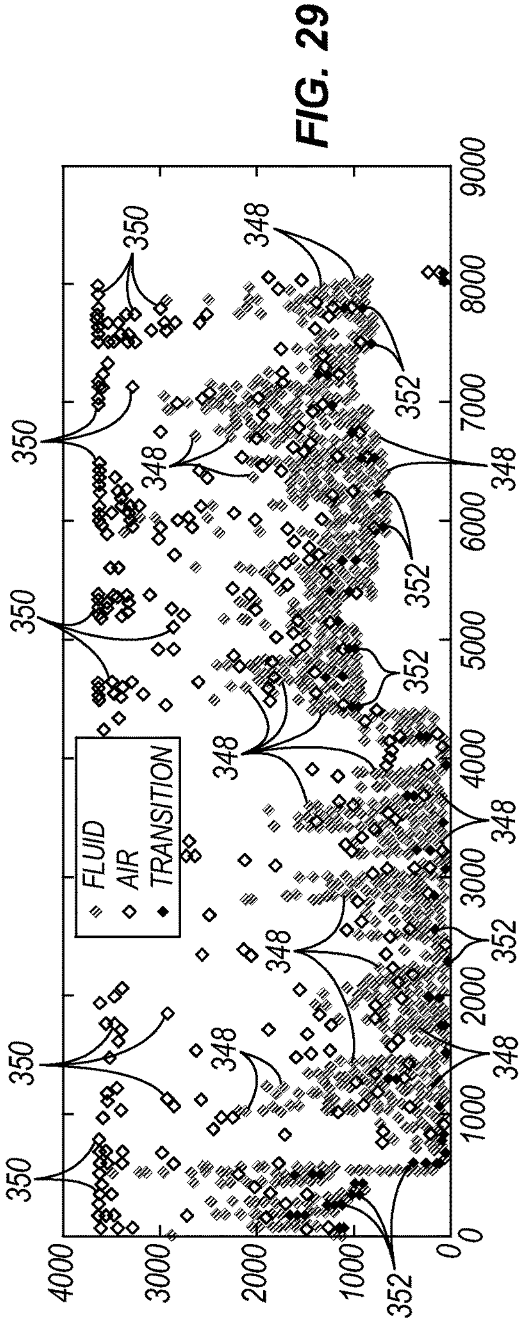
FIG. 29 illustrates a graph plotting air sensor data comprising representative points for each of fluid, air, and a transition.

FIG. 29 illustrates a graph plotting air sensor data comprising representative points for each of fluid 348, air 350, and transition 352. The Y axis represents an ADC count of the fluid of the chamber measured by a sensor and the X-axis represents sample number. The graph provides the observed air sensor ADC readings versus sample number over 10 aggregated runs. Each run ends with a transition from fluid to air. The fluid readings (hashed symbols) 348, are clearly differentiated from those associated with air (open symbols)

350. Points that are close to or on a transition region from air to fluid are marked by solid symbols 352.

Figure 30:
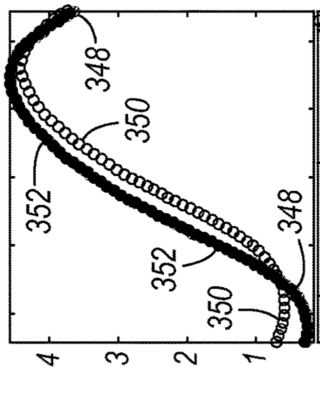
FIG. 30 illustrates a graph plotting average force profiles on the plunger corresponding to the embodiment of FIG. 32 for each of fluid, air, and a transition.
Figure 32:
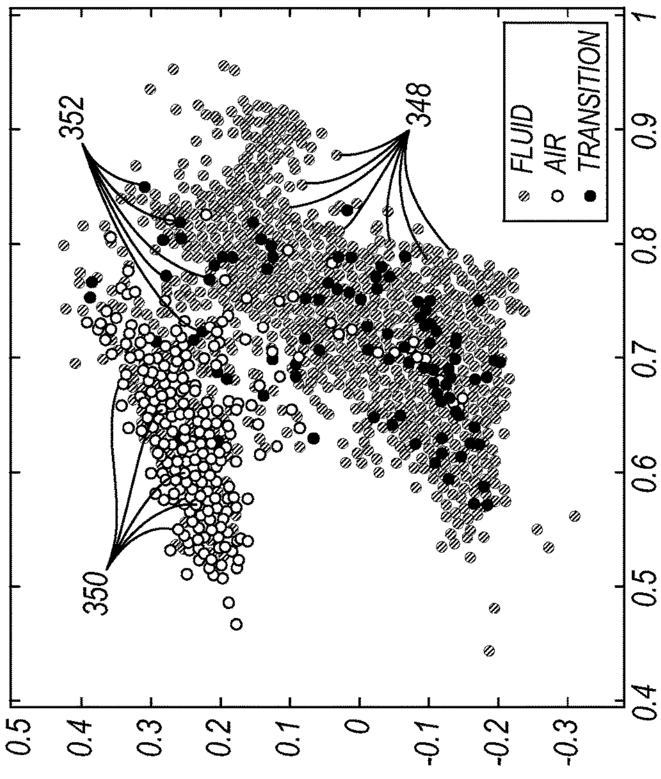
FIG. 32 illustrates a graph applying a principal component analysis plotting representative points at an infusion rate of 1,000 milliliters per hour.

FIG. 30 illustrates a graph plotting force average profiles on the plunger corresponding to the embodiment of FIG. 32 for each of fluid 348, air 350, and transition 352. The graph demonstrates systematic differences in the average force associated with the three states (fluid 348, air 350, and transition 352) of FIG. 29. The Y-axis represents force and the X-axis represents an angular position of the motor powering the plunger.

Figure 31:
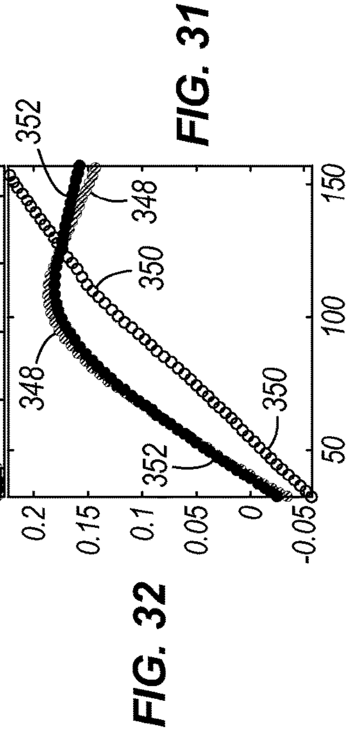
FIG. 31 illustrates a graph plotting derivatives of the force profiles on the plunger corresponding to the embodiment of FIGS. 30 and 32 for each of fluid, air, and a transition.

FIG. 31 illustrates a graph plotting derivatives of the force profiles on the plunger corresponding to the embodiment of FIGS. 30 and 32 for each of fluid 348, air 350, and transition 352. The Y-axis represents a derivative of the force and the X-axis represents an angular position of the motor powering the plunger. The graph demonstrates that the systematic differences between the three states of FIG. 32 can be enhanced and differentiated from mechanism specific variation through the application of the first derivative.

FIG. 32 illustrates a graph applying a principal component analysis to plot representative points at an infusion rate of 1,000 milliliters per hour, with hashed symbols representing fluid points 348, open symbols representing points associated with air 350, and solid points representing transitional (indeterminant) points 352. The Y-axis represents score 4 and the X-axis represents score 2. The two dimensional view provided in the plot demonstrates a good separation across multiple actuators, fluids, and sets.

Figure 33:
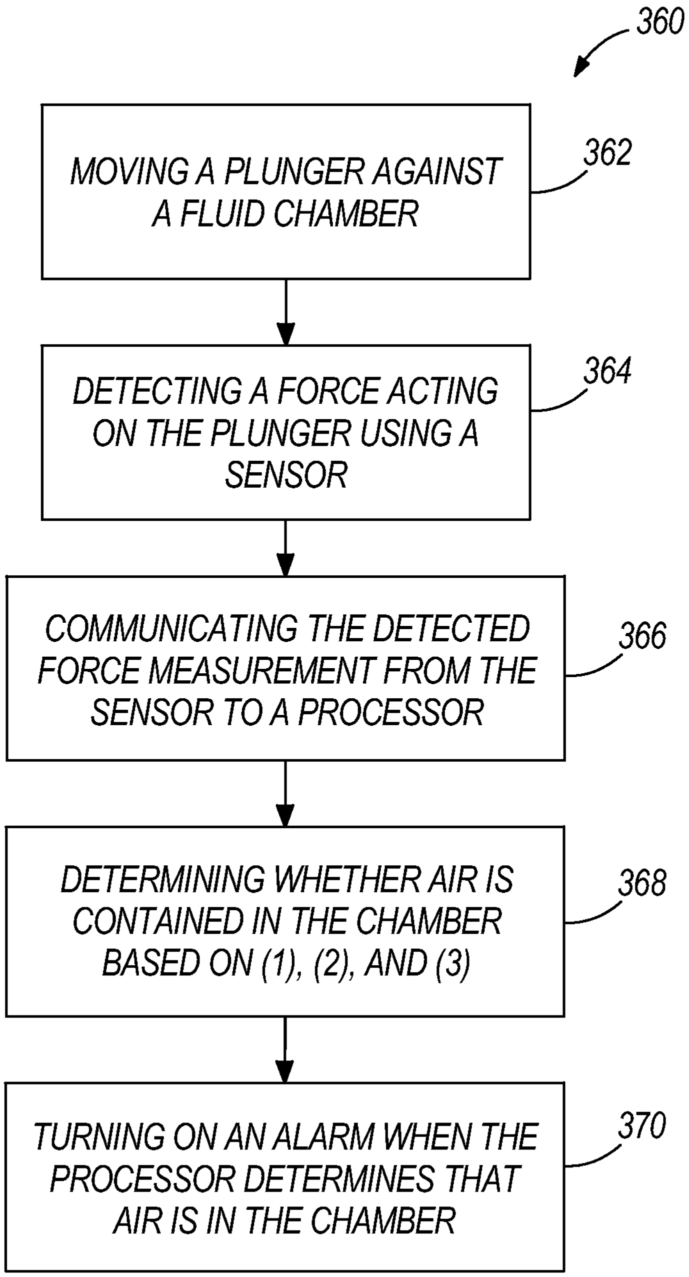
FIG. 33 illustrates a flowchart for one embodiment of a method for detecting air in a chamber of an infusion system.

FIG. 33 illustrates a flowchart for one embodiment of a method 360 for detecting air in a chamber of an infusion system. The method 360 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 360, and the alarm being turned on if the processor determines that air is contained in the chamber which may trigger the pump being shut down. Moreover, the method 360 may utilize the clock of the drug delivery infusion system 100 of FIG. 1 to keep time of activities of the plunger or the sensor, and may use the positional sensor to determine a position of the plunger, with each being in electronic communication with the processor. In other embodiments, the method 360 may utilize varying components to implement the method.

In step 362 a plunger is moved, with an actuator device, against a chamber containing fluid. In step 364 a sensor is used to detect a force acting on the plunger as it moves against the chamber. In step 366 a measurement of the force is electronically communicated from the sensor to a processor. In step 368 the processor: (1) preprocesses a force profile detected by the sensor; (2) extracts features from the force profile; and (3) classifies the force profile as being an air force profile or a liquid force profile based on the extracted features of the force profile. In step 370 the processor turns on an alarm when the processor determines that the chamber contains the air. Step 370 may further comprise shutting down the pump when the alarm is turned on.

In one embodiment, the processor classifies the force profile as being the air force profile or the liquid force profile without applying signal normalization to normalize to a baseline force profile. In another embodiment, the processor further applies a signal normalization to normalize the force profile relative to a baseline force profile. In an additional embodiment, the processor preprocesses the force profile detected by the sensor by: acquiring the force profile; re-sampling the force profile for a set of angles; selecting a sub-set of angles for the force profile; and calculating a derivative of the force profile based on the force profile at the sub-set of angles. In still another embodiment, the processor preprocesses the force profile detected by the sensor by: acquiring the force profile; applying a low pass filter to the force profile; re-sampling the force profile for a set of angles; applying a range limit to the force profile; and calculating a difference of the force profile.

In another embodiment, the processor extracts the features from the force profile by at least one of calculating scores of the force profile or applying a linear discriminate analysis to the force profile. In yet another embodiment, the processor calculates the scores of the force profile by multiplying a derivative of the force profile by a set of eigenvectors, and applies the linear discriminate analysis by multiplying the scores by weights. In an additional embodiment, the processor extracts the features from the force profile using an equation L=D*(M*W)−D*M*W, wherein L=a linear discriminate analysis, D=a derivative, M=a set of eigenvectors, and W=weights. In another embodiment, the processor classifies the force profile as being the air force profile or the liquid force profile based on means of a linear discriminate analysis applied to the force profile. In other embodiments, any of the steps of the method 360 may be altered, not followed, or additional steps may be added.

In another embodiment, features of the force profile are determined preferably on the basis of force changes versus displacement or position but may also be calculated on the basis of time. The features are a characteristic of the profile that is related to the presence of air or other condition that is desired to be known. For example, features may include: the scores from an abstract factor analysis, such as principal components analysis (PCA); the peak magnitude of the force profile; the phase shift with respect to time or position of the force profile; the maximum or minimum value of the first derivative with respect to position; the correlation coefficient of the force profile with exemplary profiles representing air and fluid; the distance (e.g., Euclidean or Mahalanobis distance) between the observed profile and a set of template profiles; ratios and/or differences between one or more points or averaged regions in the force profile; the correlation between the force profile and additional sensor readings (e.g., proximal and distal pressure); variance of the force profile from the mean; and a difference of the force profile from the mean.

Additionally, the features may be viewed as a set of residuals which represent the difference between the force profile or the derivative of the force profile and the expected value. The expected value may be determined using adaptive filtering, such as Kalman filtering, or as a moving or exponentially weighted moving average. In this scheme, a set of channels are defined which represent the observed force profile at a particular position through time. One or more channels are subjected to analysis through time to detect changes in their expected level on the basis of a model, an averaged profile, and/or a problematic network. When either the residual level exceeds a pre-determined threshold or the probability of an air/fluid transition increases beyond a set level, air is indicated in the pumping chamber.

In the case of the derivative based algorithm, an alternate embodiment involves a series of channels as describe above. Each channel is separately filtered through time using a moving average, spike rejection filter and/or a lowpass filter. This provides a multiplicity of signals that vary through time. The set of signals is then subject to the derivative based algorithm in which change detection occurs using an event detection and change confirmation method, as described previously. Since each channel provides an indication of the fluid chamber status, a method is employed to combine the indicators and provide one final indicator. The preferred method is to always utilize the channel that provides the reading that is most associated with air. For example, this may comprise the channel that experienced the high derivative and greatest change through time. Alternately, aggregation of the signals can occur using a voting algorithm, fuzzy logic, decision trees, support vector machines or Bayesian networks.

In another embodiment, the multiple channels described above may be subjected to an N-th order Kalman filter and used to generate a residual from an expected value. A change is detected when the residual exceeds a pre-set threshold. In other embodiments, other methods may be utilized.

Figure 34:
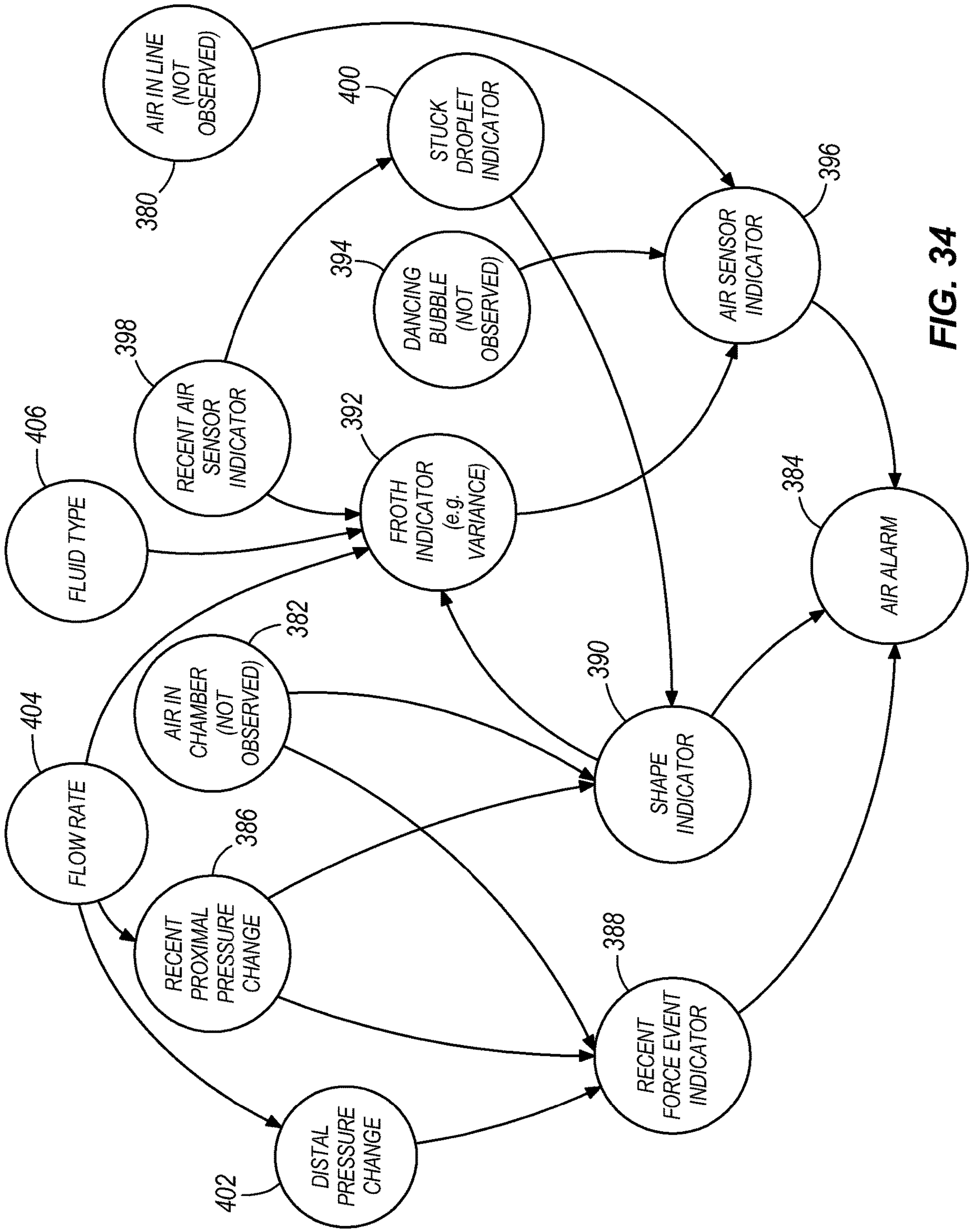
FIG. 34 illustrates a flowchart of a Bayesian network showing a combination of algorithm sensors and a priori information which may be used to produce an indication of air-in-line or air in a chamber.

FIG. 34 illustrates a flowchart of a Bayesian network showing a combination of algorithm sensors and a priori information which may be used to produce an indication of air-in-line or air in a chamber. For instance, any of the following air devices, tests, or algorithms may be utilized individually or collectively in different numbers or weights to identify air-in-line 380 or air in the chamber 382 to sound an air alarm 384: a recent proximal pressure change 386; a recent force event indicator 388; a shape indicator 390; a froth indicator (e.g. variance) 392; a dancing bubble indicator 394; an air sensor indicator 396; a recent air sensor indicator 398; a stuck droplet indicator 400; a distal pressure change 402; a flow rate 404; or a fluid type 406. In conjunction with these different tests, the following patents and patent applications are hereby incorporated by reference in full: U.S. Pat. No. 7,981,082; U.S. Ser. No. 61/460,766; and U.S. Ser. No. 61/525,587. The systems, methods, and algorithms/tests of any of the listed incorporated by reference patents may be utilized in conjunction with the systems, methods, and algorithms/tests of the instant disclosure. For example, the air indicator or air alarm as described herein may be used to qualify alarms from other sensors and thereby reduce the probability of nuisance alarms.

One or more systems/methods of the disclosure more accurately detects air in the line of an infusion device than many current systems and methods. The systems/methods of the disclosure may be combined with existing systems/methods for detecting air in an infusion system to improve the reliability of air detection systems. The disclosure allows for the combination of the output of a force sensor signal with one or more air sensors to improve the reliability of existing air detection systems/methods. In doing so, the disclosed system/method does not require additional hardware modifications but instead leverages the acquired force signal. Additionally, the disclosure does not necessarily require the replacement of existing software modules for air detection but adds an additional safety layer to improve the robustness of existing air detection systems and methods.

It should be understood, of course, that the foregoing relates to exemplary embodiments of the disclosure and that modifications may be made without departing from the scope of the disclosure as set forth in the following claims.

What is claimed is:

1. A method for detecting air in a chamber of an infusion system comprising:

moving a plunger against the chamber containing fluid;

detecting a force acting on the plunger as it moves against the chamber;

preprocessing a force profile based on the detected force acting on the plunger;

extracting features from the force profile; and classifying the force profile as being an air force profile or a liquid force profile based on the extracted features, wherein the preprocessing comprises: acquiring the force profile; re-sampling the force profile for a set of angles; selecting a sub-set of angles for the force profile; and calculating a derivative of the force profile based on the force profile at the sub-set of angles.

2. The method of claim 1, wherein the classification of the force profile as being the air force profile or the liquid force profile is done without applying signal normalization to normalize to a baseline force profile.

3. The method of claim 1, wherein the pre-processing comprises: applying a low pass filter to the force profile; applying a range limit to the force profile; and calculating a difference between the force profile and a baseline or mean force profile.

4. The method of claim 1, wherein the extraction of the features comprises calculating scores of the force profile or applying a linear discriminate analysis to the force profile.

5. A system for detecting air in a chamber of an infusion system, the system comprising one or more hardware processors configured to:

detect a force acting on a plunger as it moves against the chamber containing fluid;

preprocess a force profile based on the detected force acting on the plunger;

extract features from the force profile; and classify the force profile as being an air force profile or a liquid force profile based on the extracted features, wherein the preprocessing comprises: acquiring the force profile; re-sampling the force profile for a set of angles; selecting a sub-set of angles for the force profile; and calculating a derivative of the force profile based on the force profile at the sub-set of angles.

6. The system of claim 5, wherein the classification of the force profile as being the air force profile or the liquid force profile is done without applying signal normalization to normalize to a baseline force profile.

7. The system of claim 5, wherein the pre-processing comprises: applying a low pass filter to the force profile; applying a range limit to the force profile; and calculating a difference between the force profile and a baseline or mean force profile.

8. The system of claim 5, wherein the extraction of the features comprises calculating scores of the force profile or applying a linear discriminate analysis to the force profile.

9. A non-transitory storage medium comprising instructions when executed by one or more hardware processors cause for detecting air in a chamber of an infusion system, the one or more hardware processors configured to implement a process comprising:

detecting a force acting on a plunger as it moves against the chamber containing fluid;

preprocessing a force profile based on the detected force acting on the plunger; extracting features from the force profile; and classifying the force profile as being an air force profile or a liquid force profile based on the extracted features, wherein the preprocessing comprises: acquiring the force profile; re-sampling the force profile for a set of angles; selecting a sub-set of angles for the force profile; and calculating a derivative of the force profile based on the force profile at the sub-set of angles.

10. The non-transitory storage medium of claim 9, wherein the classification of the force profile as being the air force profile or the liquid force profile is done without applying signal normalization to normalize to a baseline force profile.

11. The non-transitory storage medium of claim 9, wherein the preprocessing comprises: applying a low pass filter to the force profile.

12. The non-transitory storage medium of claim 9, wherein the preprocessing comprises: applying a range limit to the force profile.

13. The non-transitory storage medium of claim 9, wherein the preprocessing comprises: calculating a difference between the force profile and a baseline or mean force profile.

14. The non-transitory storage medium of claim 9, wherein the extraction of features comprises calculating scores of the force profile or applying a linear discriminate analysis to the force profile.

* * * * *